(12) United States Patent
Nishikawa et al.

(10) Patent No.: US 10,154,915 B2
(45) Date of Patent: Dec. 18, 2018

(54) ACTUATOR CONTROL SYSTEM AND RELATED METHODS

(71) Applicant: Arizona Board of Regents acting for and on behalf of Northern Arizona University, Flagstaff, AZ (US)

(72) Inventors: Kiisa Nishikawa, Flagstaff, AZ (US); John Tester, Flagstaff, AZ (US); Jeremy Petak, Flagstaff, AZ (US)

(73) Assignee: Arizona Board of Regents acting for and on behalf of Northern Arizona University, Flagstaff, AZ (US)

( * ) Notice: Subject to any disclaimer, the term of this patent is extended or adjusted under 35 U.S.C. 154(b) by 509 days.

(21) Appl. No.: 14/880,118

(22) Filed: Oct. 9, 2015

(65) Prior Publication Data

US 2016/0030202 A1 Feb. 4, 2016

Related U.S. Application Data

(63) Continuation-in-part of application No. 13/203,185, filed as application No. PCT/US2010/000706 on Mar. 8, 2010, now Pat. No. 9,222,559.
(Continued)

(51) Int. Cl.
*A61F 2/70* (2006.01)
*A61F 2/66* (2006.01)
(Continued)

(52) U.S. Cl.
CPC .............. *A61F 2/70* (2013.01); *A61F 2/6607* (2013.01); *A61F 2/68* (2013.01);
(Continued)

(58) Field of Classification Search
CPC ........ A61F 2002/607; A61F 2002/6657; A61F 2002/6664; A61F 2002/701;
(Continued)

(56) References Cited

U.S. PATENT DOCUMENTS 5,383,939 A * 1/1995 James ...................... A61F 2/64
188/317
6,243,624 B1 6/2001 Wu et al.
(Continued)

OTHER PUBLICATIONS

Hae-Won Park, K. Sreenath, J.W. Hurst, J.W. Grizzle, "Identification of a Bipedal Robot with a Compliant Drivetrain," Control Systems, IEEE, vol. 31, No. 2, pp. 63-88, published Apr. 2011.
(Continued)

*Primary Examiner* — Muhammad S Islam
(74) *Attorney, Agent, or Firm* — IPTechLaw

(57) ABSTRACT

An actuator control system includes a motorized joint having first and second members rotatable relative to one another. An actuator is coupled with the motorized joint and is configured to rotate the first member relative to the second member in response to an input including a voltage, a current, or any combination thereof. A controller is coupled with the actuator and is configured to control the input using a control algorithm. The control algorithm controls the input based upon a mathematical model of biological muscle actuation that models titin as a filament which winds around actin during muscle actuation. In implementations the mathematical model includes mathematical representations of a contractile element, a viscous damping element in parallel with the contractile element, and a spring in series with the contractile element through a pulley and simultaneously in parallel with the contractile element.

20 Claims, 17 Drawing Sheets

Related U.S. Application Data

(60) Provisional application No. 61/158,563, filed on Mar. 9, 2009, provisional application No. 62/210,439, filed on Aug. 26, 2015.

(51) Int. Cl.
*A61F 2/68* (2006.01)
*F16H 35/16* (2006.01)
*A61F 2/60* (2006.01)
*A61F 2/76* (2006.01)

(52) U.S. Cl.
CPC . *A61F 2002/607* (2013.01); *A61F 2002/6657* (2013.01); *A61F 2002/6664* (2013.01); *A61F 2002/701* (2013.01); *A61F 2002/704* (2013.01); *A61F 2002/7625* (2013.01); *F16H 35/16* (2013.01)

(58) Field of Classification Search
CPC .... A61F 2002/704; A61F 2/6607; A61F 2/68; F16H 35/16
See application file for complete search history.

(56) References Cited

U.S. PATENT DOCUMENTS

| | | | |
|---|---|---|---|
| 8,864,846 B2 | 10/2014 | Herr et al. | |
| 2006/0249315 A1* | 11/2006 | Herr | A61F 2/60 180/8.1 |
| 2008/0300692 A1* | 12/2008 | Moser | A61F 2/6607 623/55 |
| 2009/0222105 A1* | 9/2009 | Clausen | A61F 2/60 623/27 |
| 2009/0299480 A1* | 12/2009 | Gilbert | A61F 2/582 623/18.11 |
| 2010/0324699 A1* | 12/2010 | Herr | A61F 2/66 623/27 |
| 2013/0310979 A1 | 11/2013 | Herr et al. | |
| 2015/0127118 A1 | 5/2015 | Herr et al. | |

OTHER PUBLICATIONS

J.W. Hurst, J.E. Chestnutt, A.A. Rizzi, "An actuator with physically variable stiffness for highly dynamic legged locomotion," published at the 2004 IEEE International Conference on Robotics and Automation (ICRA '04) held between Apr. 26, 2004 to May 1, 2004, vol. 5, pp. 4662-4667.

J. Petak, N. Heckathorn, R. LeMoyne, J. Dyer, S.H. Yeo, D. Pai, J. Tester, K. Nishikawa, "Windng [sic] Filament Muscle Model for Musculo-Skeltal [sic] Simulations," published 2013 at proceedings of the 37th Annual Meeting of the American Society of Biomechanics, Omaha, NE, pp. 1-2.

J. Tester, S.H. Yeo, D. Pai, K. Nishikawa, "A new muscle model with implications for actuation and control," published 2012 at the Proceedings of the 7th Annual Dynamic Walking Conference, Pensacola Beach, FL, pp. 1-3.

M.F. Eilenberg, H. Geyer, H. Herr, "Control of a Powered Ankle—Foot Prosthesis Based on a Neuromuscular Model," Neural Systems and Rehabilitation Engineering, IEEE Transactions, vol. 18, No. 2, pp. 164-173, published Apr. 2010.

H.M. Herr, A.M. Grabowski, "Bionic ankle-foot prosthesis normalizes walking gait for persons with leg amputation," Proc. R. Soc. B. (2012) 279, 457-464, published online Jul. 13, 2011.

* cited by examiner

ACTUATOR CONTROL SYSTEM AND RELATED METHODS

CROSS REFERENCE TO RELATED APPLICATIONS

This document claims the benefit of the filing date of provisional U.S. Patent Application Ser. No. 62/210,439 (hereinafter the '439 application), entitled "Systems and Methods for Controlling Actuators Based on Emulation of Biological Actuation of Muscle," naming as first inventor Kiisa Nishikawa, which was filed on Aug. 26, 2015, now pending. This application is also a continuation-in-part application of the earlier nonprovisional U.S. Utility patent application Ser. No. 13/203,185 (hereinafter the '185 application), entitled "Elastic Motor-Spring Actuator," naming as first inventor Kiisa Nishikawa, which has a 371(c) filing date of Dec. 2, 2011, now pending, which '185 application is a U.S. national stage entry of PCT application serial number PCT/US10/00706 (hereinafter the '706 PCT application), entitled "Elastic Motor-Spring Actuator," naming as first inventor Kiisa Nishikawa, which has an international filing date of Mar. 8, 2010 and an earliest priority date of Mar. 9, 2009, now expired, which '706 PCT application claims the benefit of the filing date of provisional U.S. Patent Application Ser. No. 61/158,563 (hereinafter the '563 application), entitled "Actuator," naming as first inventor Kiisa Nishikawa, which was filed on Mar. 9, 2009, now expired. The disclosures of each of the '439 application, the '185 application, the '706 PCT application, and the '563 application are each hereby entirely incorporated herein by reference.

GOVERNMENT LICENSE RIGHTS

This invention was made with government support under grant number IIP-1237878 awarded by the National Science Foundation. The government has certain rights in the invention.

BACKGROUND

1. Technical Field

Aspects of this document relate generally to methods and systems for controlling actuators. More specific implementations involve methods and systems for controlling actuators of prosthetics, orthotics, or robotic devices.

2. Background Art

A variety of motorized actuators exist in the art, controlled by various mechanisms. A variety of prosthetics and orthotics exist for a variety of limb types to provide a user assistance with mobility and function. Some prosthetics and orthotics have motorized function, including a motorized actuator, to assist a user with movement or the like, and such motorized devices may also be used in robotics. Software may be implemented to control the motorized function of a motorized actuator, whether used for a prosthetic/orthotic, in a robotic environment, or in some other environment.

SUMMARY

Implementations of actuator control systems may include: a motorized joint having a first member and a second member rotatable relative to the first member; an actuator coupled with the motorized joint and configured to rotate the first member relative to the second member in response to an input including one of a voltage, a current, and any combination thereof, and; a controller coupled with the actuator and configured to control the input using a control algorithm; wherein the control algorithm controls the input based upon a mathematical model of biological muscle actuation that models titin as a filament which winds around actin during muscle actuation.

Implementations of actuator control systems may include one, all, or any of the following:

The mathematical model may model an N2A region of titin binding to actin during muscle actuation.

The mathematical model may include mathematical representations of a contractile element, a viscous damping element in parallel with the contractile element, and a spring in series with the contractile element through a pulley and simultaneously in parallel with the contractile element.

The actuator control system may include a sensor configured to sense a state of the motorized joint from among a plurality of states, and the controller may control the input based upon a sensed state.

The plurality of states may include a standing state, a controlled plantar flexion state, a controlled dorsiflexion state, a powered plantar flexion state, an early swing state, and a late swing state.

Implementations of actuator control systems may include: a motorized joint including a first member and a second member rotatable relative to the first member; an actuator coupled with the motorized joint and configured to rotate the first member relative to the second member in response to an input including one of a voltage, a current, and any combination thereof, and; a controller coupled with the actuator and including a control algorithm including a mathematical model of biological muscle actuation that includes mathematical representations of: a contractile element; a viscous damping element in parallel with the contractile element, and; a spring (titin spring) in series with the contractile element through a pulley and simultaneously in parallel with the contractile element; wherein the controller may be configured to generate the input using the mathematical model and data from one or more sensors coupled with the motorized joint.

Implementations of actuator control systems may include one, all, or any of the following:

The mathematical model may define a muscular force ($F_m$) of a muscle tendon unit (MTU) as $F_m = k_{ss}(X_m - X_p) = k_{ts} X_{ts} + F_{ce} + c_{ce} \dot{X}_{ce}$, where $k_{ss}$ is a spring rate of a series spring, $X_m$ is a change in length of the MTU, $X_p$ is a change in length of the viscous damping element, $k_{ts}$ is a spring rate of the titin spring, $X_{ts}$ is a change in length of the titin spring, $F_{ce}$ is a force of the contractile element, $c_{ce}$ is a damping rate of the contractile element, and $\dot{X}_{ce}$ is a damper velocity of the viscous damping element.

The spring of the mathematical model may include an exponential spring.

The mathematical model may further include a mathematical representation of a second spring in series with the viscous damping element and attached to an axle of the pulley.

The mathematical model may further include a mathematical representation of a clutch configured to selectively prevent rotation, but not translation, of the pulley.

The viscous damping element may include a damping rate that is related to a muscle activation level.

The viscous damping element may include a bi-directional damping rate.

Implementations of actuator control systems may include: a foot-ankle prosthesis having a joint, the joint rotatably coupling a first member with a second member; an actuator coupled with the foot-ankle prosthesis and configured to cause dorsiflexion and plantar flexion of the foot-ankle prosthesis by rotating the first member relative to the second member in response to an input including one of a voltage, a current, and any combination thereof, and; a controller coupled with the actuator and configured to generate the input using a control algorithm; wherein the control algorithm may be based upon a mathematical model of biological muscle actuation that models titin as a filament which winds around actin during muscle actuation.

Implementations of actuator control systems may include one, all, or any of the following:

The mathematical model may model an N2A region of titin binding to actin during muscle actuation.

The mathematical model may include a mathematical representation of a virtual anterior muscle for effecting dorsiflexion and a virtual posterior muscle for effecting plantar flexion, the virtual posterior muscle modeled after a combination of a soleus muscle and a gastrocnemius muscle.

The mathematical model may be configured to, using a sensed ankle angular position: calculate a length of the virtual anterior muscle, calculate a length of the virtual posterior muscle, calculate a force produced by the virtual anterior muscle, and calculate a force produced by the virtual posterior muscle.

The mathematical model may be configured to calculate a net ankle torque using the calculated force produced by the virtual anterior muscle and the calculated force produced by the virtual posterior muscle and, using the calculated net ankle torque, generate the input.

The mathematical model may include a value representing a muscle activation level of the virtual anterior muscle, a value representing a muscle activation level of the virtual posterior muscle, a value related to an attachment parameter of the virtual anterior muscle, and a value related to an attachment parameter of the virtual posterior muscle.

The mathematical model may model a non-linear relationship of muscle force to muscle length during muscle stretch and during muscle shortening.

The mathematical model may model powered plantar flexion activation in relation to an angular velocity of the first member relative to the second member during controlled dorsiflexion.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

Figure 1:
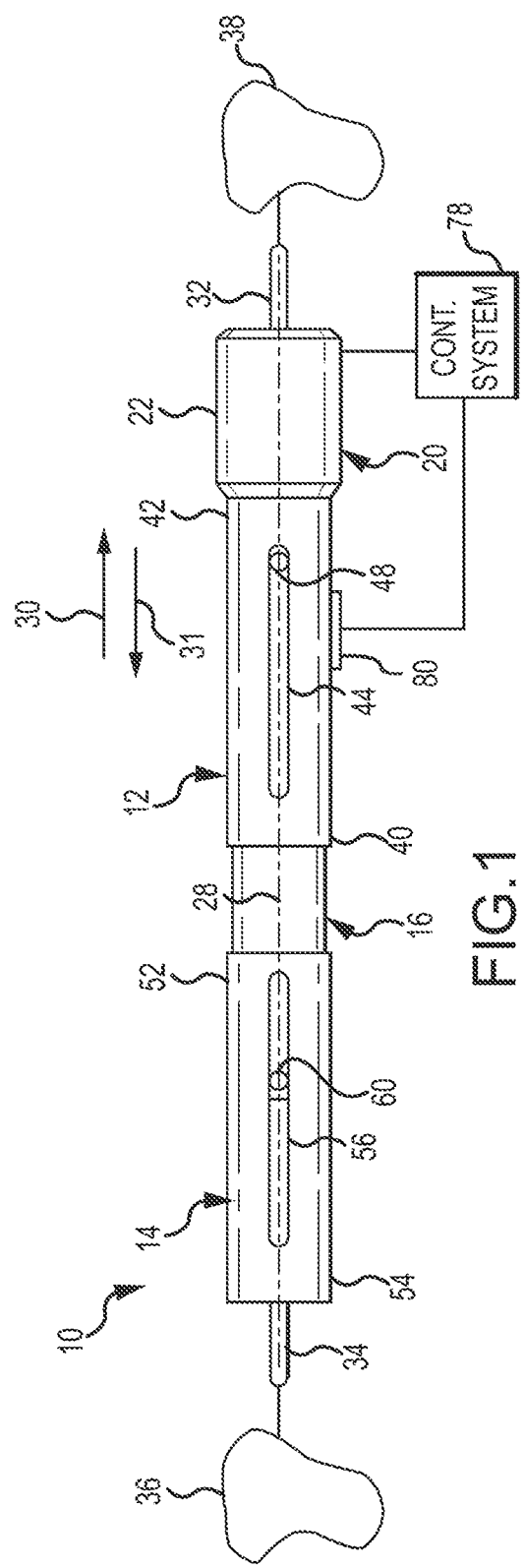
FIG. 1 is a plan view of a first embodiment of an actuator.

This disclosure, its aspects and implementations, are not limited to the specific components, assembly procedures or method elements disclosed herein. Many additional components, assembly procedures and/or method elements known in the art consistent with the intended actuator control systems and related methods will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such actuator control systems and related methods, and implementing components and methods, consistent with the intended operation and methods.

A first embodiment 10 of an elastic motor-spring actuator is illustrated in FIGS. 1-4 and may comprise a fixed member 12 and a free member 14. The fixed and free members 12 and 14 are operatively connected together so that the free member 14 is moveable with respect to the fixed member 12. In the embodiment 10 shown in FIGS. 1-4, the fixed and free members 12 and 14 are operatively connected together by a connector member 16. Alternatively, the fixed and free members 12 and 14 can be operatively connected together without a connector member 16, such as, for example, as in the case of a second embodiment 210, illustrated in FIGS. 6-11.

Figure 2:
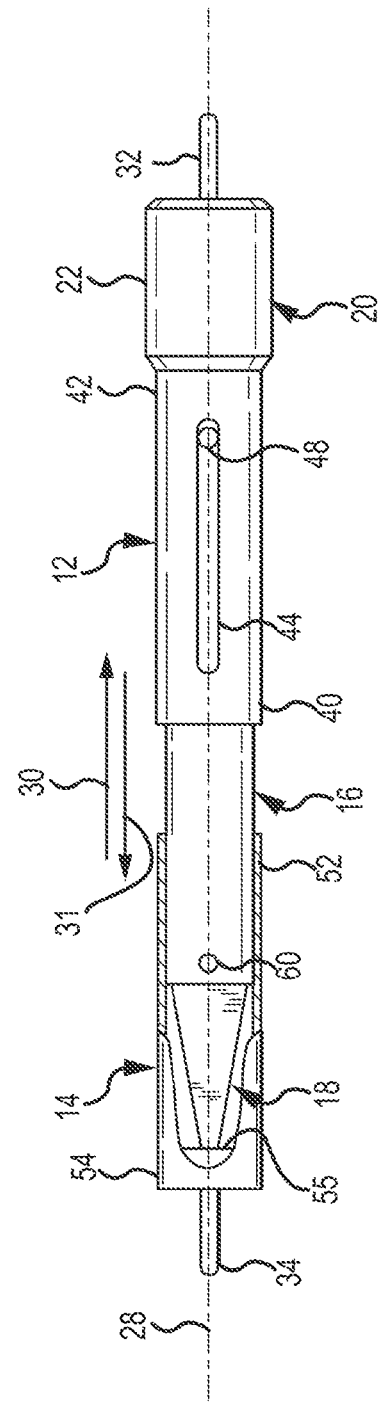
FIG. 2 is a plan view of the actuator illustrated in FIG. 1 with a portion of the free member broken away to show the elastic element.

The actuator 10 may also comprise an elastic element 18 that is operatively associated with the fixed and free members 12 and 14, as best seen in FIG. 2. In the first embodiment 10, the elastic element 18 is connected to the fixed member 14 via the connector member 16. Alternatively, other arrangements, such as the arrangement of the second embodiment 210, are also possible for operatively connecting the fixed and free members 12 and 14 with an elastic element 18.

Figure 3:
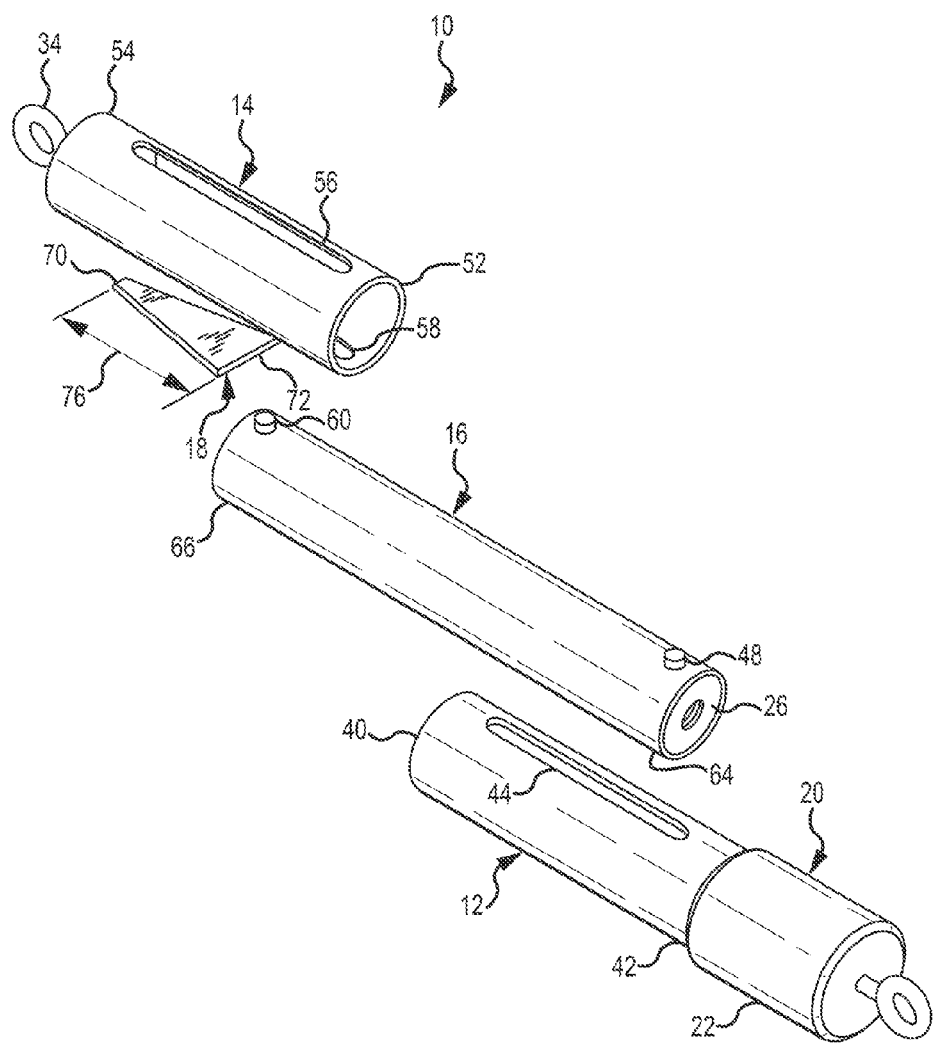
FIG. 3 is an exploded perspective view of the first embodiment of the actuator showing the various components thereof.

As will be described in much greater detail herein, elastic element 18 provides actuator 10 with a degree of compliance or springiness. In certain embodiments, the degree of compliance can be changed or tuned as may be desired for the particular application. In addition, the compliance of actuator 10 may be changed or varied depending on the degree of force that is provided on (or exerted by) actuator 10. In one embodiment, elastic element 18 may comprise a trapezoidal configuration, as best seen in FIGS. 2 and 3. The trapezoidal configuration causes the elastic element 18 to elongate non-linearly in response to a given force, thereby providing the actuator 10 with a non-linear compliance. Alternatively, other configurations for elastic element 18 are possible and may be used to provide actuator 10 with any of a wide range of compliance characteristics.

Actuator 10 may also comprise a drive system 20 that is operatively associated with the fixed and free members 12 and 14. Drive system 20 provides a means for moving the free member 14 with respect to the fixed member 12 and may comprise a variety of components and elements suitable for providing this function. By way of example, in the embodiment 10 illustrated in FIGS. 1-4, drive system 20 may comprise a motor 22 mounted to fixed member 12. Motor 22 is operatively connected to a lead screw 24. A nut 26 mounted to connector member 16 engages lead screw 24. Rotation of lead screw 24 by motor 22 causes nut 26, thus connector member 16, to move or translate along a longitudinal axis 28 of actuator 10, i.e., generally in the directions indicated by arrows 30 and 31. See FIGS. 1 and 2.

The fixed and free members 12 and 14 of actuator 10 also may be configured to attach to the particular load that is to be acted on by actuator 10. For example, in the embodiment illustrated in FIGS. 1-4, actuator 10 may be provided with respective mounting lugs or rings 32 and 34 to allow the actuator 10 to be operatively connected to a load, i.e., moveable device or object 36, that is to be acted on by actuator 10. For example, in one example configuration, first ring 32 may be attached or connected to a fixed object 38, whereas second ring 34 may be attached or connected to the moveable object 36.

Actuator 10 may be operated as follows to act on a load, such as an object 36 attached to ring 34. Generally speaking, actuator 10 will be used to provide a pulling or contraction force (i.e., a force in the direction of arrow 30) to the moveable object 36, although the actuator 10 may also be used to provide an extension force (i.e., in the direction of arrow 31). Depending on the relative initial position of the moveable object 36, as well as on the initial length of actuator 10, elastic element 18 may be slightly stretched or elongated at an initial condition. That is, the actuator 10 may be pre-loaded, applying a slight contractile force to the moveable object 36.

Additional contractile force can be applied to the object 36 by operating the drive system 20. More specifically, motor 22 will rotate the lead screw 24 in a direction that will cause the nut 26 (FIGS. 3 and 4) to move in direction 30. The movement of nut 26 will cause the connector member 16 and free member 14 to move in direction 30 as well. As the connector member 16 moves in direction 30, it pulls on free member 14 via elastic element 18. Elastic element 18 extends or stretches until the force exerted on elastic element 18 equals the resistance offered by the object 36. Thereafter, moveable object 36 will move in direction 30.

In addition to the application of a contraction force, i.e., a force in the direction of arrow 30, actuator 10 may be operated to apply to object 36 an extension force, i.e., a force in the direction of arrow 31. Application of the extension force may be accomplished by reversing the direction of motor 22. To the extent that elastic element 18 is stretched or elongated during the contraction cycle, movement of the actuator 10 in the extension direction 31 will be assisted by the energy stored in elastic element 18. If the elastic element 18 becomes fully relaxed, continued rotation of lead screw 24 will cause the connector module 16 to continue to move in direction of arrow 31, until pins 60 and 62 contact the ends of respective slots 56 and 58. At this point, continued movement of connector module 16 will result in corresponding movement of free member 14 in the direction of arrow 31.

Various embodiments may be operated in a manner that closely simulates biological muscle contraction. Consequently, actuators may be used to advantage in a wide range of fields and applications, including the fields of robotics and prosthetics. More particularly, actuators may be operated in accordance with a "winding filament" or "winding spring" model for how the protein titin contributes to biological muscle contraction. Stated another way, an actuator like those disclosed herein does not function simply as a linear motor, but includes an elastic energy storage element as well. The elastic element is capable of changing its compliance automatically in order to maximize the work done by the actuator. That is, not only can the drive system do work on the elastic element, but the elastic element may do work on the drive system, speeding the return or recoil of the actuator.

Moreover, and like the titin model, the actuator disclosed herein is capable of storing elastic energy without a change in overall length of the actuator. In addition, the change in length and compliance of the actuator is tunable and further these characteristics (i.e., length and compliance) may differ depending on whether the actuator is shortening or contracting while energized or passively recoiling due to the return of elastic energy from the elastic element. The elastic element exhibits recoil during fast unloading and exhibits a tuneable non-linear relationship between the magnitude of the load and the compliance of the actuator. The overall characteristics of the actuator are such that the actuator becomes less compliant with stronger contraction forces and more compliant with weaker contraction forces.

Having briefly described one embodiment of the actuator, as well as some of its more significant features and advantages, various exemplary embodiments of actuators will now be described in detail. However, before proceeding with the detailed description, it should be noted that, while the various embodiments are shown and described herein as they might be used in certain operational scenarios to act on and move object 36 with respect to another object 38, actuators may be used in a wide range of applications and in a wide range of operational scenarios, as would become apparent to persons having ordinary skill in the art after having become familiar with the teachings provided herein. Consequently, the various systems disclosed herein should not be regarded as limited to the particular embodiments, devices, and operational scenarios shown and described herein.

Referring back now to FIG. 1, a first embodiment 10 of actuator embodiment may comprise a fixed or contractile module 12 and a free or compliant module 14. A connector member or module 16 operatively connects the contractile and compliant modules 12 and 14 together so that the compliant module 14 can move with respect to the contractile module 12.

Before proceeding with the description, it should be noted that, as used herein, the terms "fixed" and "free" are used for convenience in referring to those components of the actuator that, in the embodiments described herein, are generally "fixed" and "free" during normal actuator operation. That is, in a typical application, the fixed member 12 of actuator 10 is attached to an object or device that will remain stationary during actuator operation, whereas the free member 14 will be attached to an object or device that is to be moved (or acted on) by actuator 10. However, in an alternative arrangement, the free member 14 of actuator 10 could be connected to a "fixed" (i.e., immovable) object, in which case it could be referred to in such an alternative arrangement as the "fixed" member. In still another arrangement, both ends of actuator 10 could be connected to moveable objects, i.e., both ends of actuator 10 may move relative to some arbitrary fixed reference frame.

However, because persons having ordinary skill in the art would appreciate this difference and would readily understand that the fixed and free members 12 and 14 of actuator 10 may not necessarily be "fixed" and "free" in any particular application, the following description will continue to use the terms "fixed" and "free" as a matter of convenience without being limited to whether the fixed and free members 12 and 14 are truly "fixed" and "free" in a particular actuator application.

Continuing now with the description, in the embodiment shown and described herein, the fixed member 12 may comprise a generally elongate, tubular structure having a proximal end 40 and a distal end 42 that is sized to slidably receive the connector member or module 16, as best seen in FIGS. 1 and 2. Because the fixed member 12 generates the forces for contraction and elongation, i.e., forces in the directions of arrows 30 and 31, respectively, via rotation of lead screw 24, it may be referred to herein in the alternative as "contractile module" 12.

Figure 4:
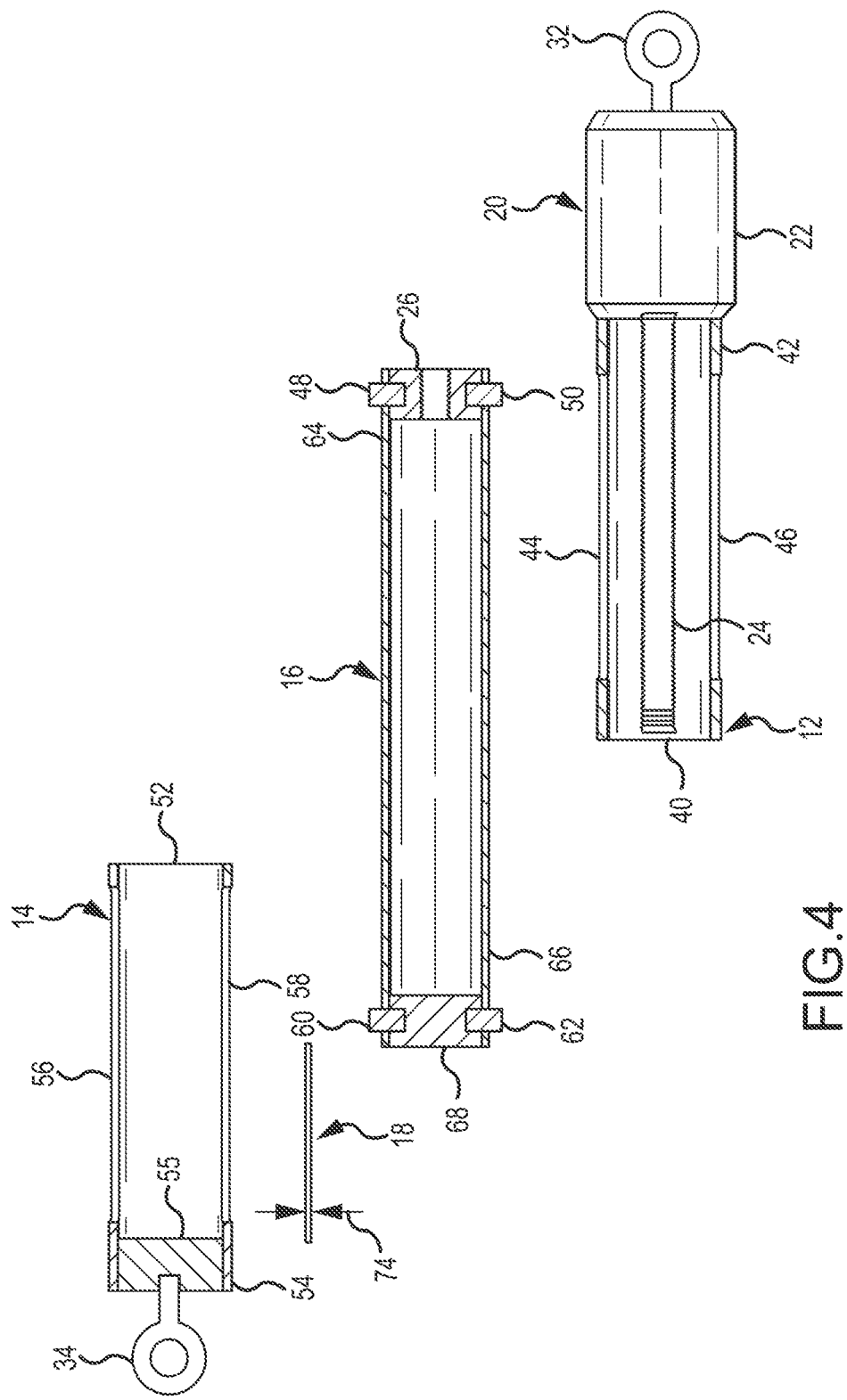
FIG. 4 is an exploded sectional view in elevation of the actuator components illustrated in FIG. 3.

Contractile module 12 may be provided with a pair of elongated slots 44 and 46, as best seen in FIG. 4. Elongated slots 44 and 46 are sized to slidably receive respective pins 48 and 50 provided on a first end 64 of connector member 16. See FIGS. 1, 2, and 4. The engagement of the pins 48 and 50 with respective slots 44 and 46 allows the connector member 16 to slide back and forth along axis 28, i.e., generally in the directions of arrows 30 and 31, as best seen in FIGS. 1 and 2. The engagement of pins 48 and 50 with slots 44 and 46 limits the axial movement or travel of the connector module 16 and also prevents the connector member 16 from rotating with respect to contractile module 12. Distal end 42 of contractile module 12 may be configured to receive the motor 22 and lead screw 24 of drive system 20 in the manner that will be described in greater detail below.

Contractile module 12 may be fabricated from any of a wide range of materials (e.g., metals or plastics) that are now known in the art or that may be developed in the future that are, or would be, suitable for use in the intended application. Consequently, embodiments should not be regarded as limited to a contractile module fabricated from any particular material. However, by way of example, in one embodiment, contractile module 12 is fabricated from acrylic plastic. In another embodiment, the contractile module 12 is fabricated from brass.

Free member 14 is similar in certain respects to the fixed member 12 and may also comprise a generally elongate, tubular structure having a proximal end 52 and a distal end 54, as best seen in FIGS. 1-4. As was the case for fixed member 12, free member 14 is also sized or configured to slidably receive connector member or module 16. Because free member 14 provides the compliance, recoil, and elasticity functions of actuator 10, free member 14 also may be referred to herein in the alternative as "compliant module" 14.

Compliant module 14 also may be provided with a pair of elongated slots 56 and 58 therein that are sized to receive respective pins 60 and 62 provided on a second end 66 of connector member 16. The engagement of the pins 60 and 62 with respective slots 56 and 58 allows compliant module 14 to slide back and forth along axis 28, generally in the directions of arrows 30 and 31. The engagement of pins 60, 62 and slots 56, 58 limits the travel or movement of connector module 16 with respect to compliant module 14 and also prevents the compliant module 14 from rotating with respect to connector member 16. In one embodiment, distal end 54 of compliant module 14 may be sized to receive an end cap 55. End cap 55 may be configured to receive ring 34 suitable for engaging the load or object 36. Alternatively, other structures and arrangements may be used to operatively connect the compliant module 14 to the load or object 36, as would become apparent to persons having ordinary skill in the art after having become familiar with the teachings provided herein. Consequently, embodiments should not be regarded as limited to any particular arrangement or structure for connecting the actuator 10 to the load.

Compliant module 14 also may be fabricated from any of a wide range of materials (e.g., metals or plastics) now known in the art or that may be developed in the future that are, or would be, suitable for use in the intended application. Consequently, embodiments should not be regarded as limited to any particular material. However, by way of example, in one embodiment, compliant module 14 is fabricated from brass, although other materials, such as acrylic plastic, may be used as well.

Connector member or module 16 may comprise a generally elongate, tubular structure that is sized to be slidably received by the contractile and compliant modules 12 and 14 in the manner described above. In the particular exemplary embodiment shown and described herein, connector member or module 16 is sized to be received by the contractile and compliant modules 12 and 14 in the manner illustrated in FIGS. 1 and 2. That is, connector module 16 is sized to fit inside the contractile and compliant modules 12 and 14. Alternatively, other arrangements are possible. For example, in another embodiment, connector member 16 may be sized to receive the contractile and compliant modules. That is, connector member 16 may fit or slide over the contractile and compliant modules 12 and 14. In still another alternative arrangement, the various modules 12, 14, and 16 could comprise a "telescoping" type of arrangement, wherein the connector module 16 fits inside the contractile module 12, and wherein the compliant module 14 fits inside connector module 14, or vice-versa.

Referring now primarily to FIGS. 3 and 4, a first end 64 of connector member 16 is sized to receive nut 26. As described herein, nut 26 operatively engages the lead screw 24 provided within contractile module 12. The first end 64 of connector member 16 may also be provided with a pair of pins 48 and 50 that are configured to slidably engage the slots 44 and 46 provided in contractile module 12 in the manner already described. Alternatively, pins 48 and 50 could be provided on nut 26, as would become apparent to persons having ordinary skill in the art after having become familiar with the teachings provided herein. Accordingly, embodiments should not be regarded as limited to the particular arrangement of nut 26 and pins 48 and 50 shown and described herein.

Second end 66 of connector member 16 may be provided with an end cap 68, as best seen in FIG. 4. End cap 68 may be provided with a pair of pins 60, 62 that are configured to slidably engage the slots 56 and 58 provided on compliant module 14, in the manner already described. Alternatively, pins 60 and 62 could be otherwise provided on second end 66 of connector member 16. In addition, end cap 68 may also be provided with a suitable attachment structure or mounting lug (not shown) to allow elastic element 18 to be secured to connector member 16. See FIG. 2. Alternatively, elastic element 18 could be secured to end cap 68 by means of an adhesive.

As was the case for the contractile and compliant modules 12 and 14, connector member 16 may be fabricated from any of a wide range of materials, such as metals or plastics, that are now known in the art or that may be developed in the future that are, or would be, suitable for use in the intended application. Consequently, embodiments should not be regarded as limited to any particular material. However, by way of example, in one embodiment, connector member 16 is fabricated from aluminum. End cap 68 may likewise be fabricated from any of a wide range of materials suitable for the intended application. By way of example, in one embodiment, end cap 68 is fabricated from acrylic plastic. Alternatively, other materials could be used, as would become apparent to persons having ordinary skill in the art after having become familiar with the teachings provided herein.

Actuator 10 may also comprise an elastic element 18. As briefly described above, elastic element 18 provides the actuator 10 with compliance or springiness and also serves as an energy storage element. That is, and as will be described in greater detail below, the drive system 20 can do work on (i.e., store energy in) elastic element 18 while the actuator 10 is contracting (e.g., during a contraction cycle). In addition, the elastic element 18 can also do work on (i.e., return energy to) the drive system 20 while the actuator 10 is extending (e.g., during an extension cycle). Elastic element 18 may be configured to provide the actuator 10 with any of a wide range of compliance properties or "schedules," depending on the particular materials, shapes, and configurations of elastic element 18.

For example, and with reference now primarily to FIGS. 2 and 3, in one embodiment, elastic element 18 may comprise an elastic material having non-linear elongation properties. More particularly, elastic member 18 may comprise a thin, sheet-like member having a trapezoidal configuration wherein a first end 70 has a smaller dimension or is shorter than a second end 72. The trapezoidal configuration of elastic element 18 causes the elastic element 18 to elongate or stretch in a non-linear manner with a given force. The non-linear response of the elastic element 18 causes the compliance of the actuator 10 to vary depending on the contractile force that is applied by the actuator 10. In the particular embodiment shown and described herein, the actuator 10 will become less compliant with increased contraction forces and more compliant with decreased contraction forces.

The specific dimensions of the elastic element 18, as well as the particular material from which it may be fabricated, may be varied depending on a wide range of factors, including the particular degree of compliance and compliance variation (i.e., non-linear response) that may be required or desired in the particular application. Consequently, embodiments should not be regarded as limited to elastic elements fabricated from any particular material or having any particular dimensions. However, by way of example, in one embodiment, the elastic element 18 may comprise latex having a thickness 74 (FIG. 4) of about 0.2 mm (about 0.008 inches) and an overall length 76 of about 25 mm (about 1 inch). The length of short end 70 is about 5 mm (about 0.2 inches), whereas the length of long end 72 is about 10 mm (about 0.4 inches).

As described herein, the elastic element 18 may comprise any of a wide range of materials having any of a wide range of configurations or shapes to provide the actuator 10 with any of a wide range of compliance characteristics. An elastic element 18 comprising the trapezoidal configuration illustrated in FIGS. 2-4 is one example of an elastic element 18 that may be used. However, other arrangements and configurations are possible. For example, another embodiment may comprise an adjustable elastic element 118. Adjustable elastic element 118 may be used or implemented to provide the actuator 10 with adjustable compliance characteristics. In addition, the adjustable elastic element 118 will allow the compliance of the actuator 10 to be adjusted "on-the-fly," i.e., during actuator operation, as will be described in greater detail below.

Figure 5:
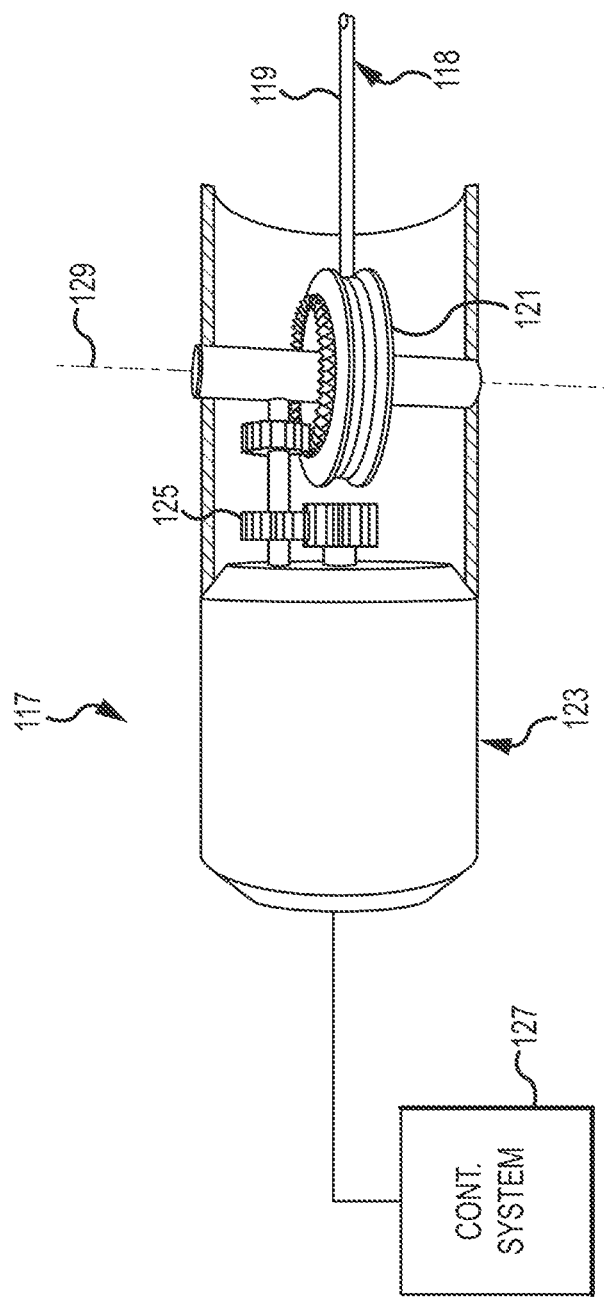
FIG. 5 is a perspective view of an adjustable elastic element that may be substituted for the elastic element illustrated in FIGS. 1-4.

Referring now primarily to FIG. 5, in another embodiment, adjustable elastic element 118 may comprise a take-up system 117 that may be used to lengthen and shorten an operating length 119 of the elastic element 118. Changing the operating length 119 of elastic element 118 will change the compliance of actuator 10. Depending on the application, the take-up system 117 may be operated before the actuator 10 is operated to provide actuator 10 with a desired degree of compliance. Alternatively, the take-up system 117 may be operated on-the-fly, i.e., during actuator operation, to dynamically change the compliance of actuator 10 during operation.

In the particular embodiment illustrated in FIG. 5, take-up system 117 may be mounted to the distal end 54 (FIGS. 1 and 2) of compliant module 14. Take-up system 117 may comprise a spool 121 operatively connected to a drive motor 123, such as, for example, via a transmission assembly 125. A control system 127 operatively connected to drive motor 123 may be used to operate drive motor 123. Drive motor 123 may be used to rotate spool 121 about axis 129 to change the operating length 119 (i.e., the operating length 119 refers to the relaxed or unstretched length of that portion of the elastic element 118 extending between spool 121 and end cap 68, not the distance between spool 121 and end cap

68 of connector module 16) of elastic element 118. Shorter operating lengths 119 of elastic element 118 will reduce the compliance of actuator 10, whereas longer operating lengths 119 will increase the compliance of actuator 10.

The various devices and components comprising take-up system 117 may comprise any of a wide range of components and devices that are now known in the art or that may be developed in the future that are (or would be) suitable for the intended application. Consequently, embodiments should not be regarded as limited to any particular components and devices. However, by way of example, in one embodiment, elastic element 118 may comprise an elastic cord fabricated from nylon-reinforced rubber and having a constant cross-section. Spool 121 may be fabricated from plastic, and motor 123 may comprise a stepper motor. Transmission system 125 may comprise a spur-gear transmission system. Control system 127 may comprise an electronic motor control system suitable for controlling the particular type of motor 123 that is to be used and that is suitable for providing the desired control functionality. Consequently, embodiments should not be regarded as limited to any particular type of motor control system 127. However, by way of example, in one embodiment, motor control system 127 comprises a stepper motor control system capable of reversibly driving stepper motor 123 in the clockwise and counterclockwise directions.

Referring back now primarily to FIGS. 1 and 4, the actuator 10 may also be provided with a drive system 20 for providing a means for moving the free member or compliant module 14 with respect to fixed member or contractile module 12. In the embodiment illustrated in FIGS. 1-4, drive system 20 may comprise a motor 22, a lead screw 24, a nut 26, and a control system 78. Motor 22 may be mounted to the distal end 42 of contractile module 12. Lead screw 24 is operatively connected to motor 22 so that motor 22 may turn or rotate lead screw 24 in the clockwise and counterclockwise directions. In the embodiment shown and described herein, lead screw 24 is mounted to motor 22 and is driven thereby by an integral transmission assembly. Alternatively, other arrangements are possible, as would become apparent to persons having ordinary skill in the art after having become familiar with the teachings provided herein. Consequently, embodiments should not be regarded as limited to the particular configuration shown and described herein.

Motor 22 may comprise any of a wide variety of motors, such as brushed or brushless dc motors, now known in the art or that may be developed in the future that are or would be suitable for the particular application. Consequently, embodiments should not be regarded as limited to any particular motor type. However, by way of example, in one embodiment, motor 22 comprises a high-speed brushed dc motor of the type well-known in the art and readily commercially available.

Lead screw 24 may comprise any of a wide variety of lead screws that are well-known in the art and that are readily commercially available. The pitch and diameter of the lead screw 24 may be selected to provide the actuator 10 with the desired speed and/or force development (i.e., mechanical advantage) characteristics, as would become apparent to persons having ordinary skill in the art after having become familiar with the teachings provided herein. By way of example, in one embodiment, lead screw 24 has a pitch of about 0.0625 mm (about 0.0025 inches) and a diameter of about 2.2 mm (about 0.09 inches). Lead screw may be fabricated from any of a wide range of materials, as would become apparent to persons having ordinary skill in the art. By way of example, in one embodiment, lead screw 24 is fabricated from steel.

As described above, connector module 16 is provided with a nut 26 that is configured to operatively engage lead screw 24. Accordingly, rotation of lead screw 24 will cause nut 26 to move back and forth along lead screw 24 in the directions indicated by arrows 30 and 31. Nut 26 is mounted to first end 64 of connector module 16 so that movement of the nut 26 along lead screw 24 results in corresponding movement of connector module 16 with respect to contractile module 12. Nut 26 may be provided with a pair of pins 48 and 50 that are sized to be slidably received by slots 44 and 46 provided in contractile module 12 in the manner already described. Alternatively, other arrangements are possible for mounting the nut 26 to the first end 64 of connector module 16. Nut 26 may be fabricated from any of a wide range of materials suitable for the intended application and the particular material used for lead screw 24. Consequently, embodiments should not be regarded as limited to any particular materials. However, by way of example, in one embodiment, nut 26 is fabricated from steel.

In the embodiment shown and described herein, nut 26 comprises a plain threaded nut sized to operatively engage lead screw 24 in the manner described herein. However, other variations are possible. For example, in another embodiment, nut 26 may comprise a ball nut assembly (not shown) wherein balls retained in the nut engage the threads on the lead screw 24. Generally speaking, ball nuts provide for a longer-wearing and lower friction engagement with a lead screw.

Motor control system 78 controls motor 22, thus the overall operation of actuator 10. That is, motor control system 78 may be used to operate actuator 10 to provide contraction and extension forces (i.e., in the directions of arrows 30 and 31, respectively), as well as to control the speed at which the actuator 10 operates.

Motor control system 78 may comprise an open-loop (i.e., without position feedback) or a closed-loop (i.e., with position feedback) control system, in which the motor 22 is controlled either with or without information relating to the kinematic parameters (i.e., position, velocity, and/or acceleration) of the nut 26, thus connector module 16. Generally speaking, it will be desirable to utilize a closed-loop motor control system 78. Information regarding the position of the connector module 16 may be provided by a linear encoder (not shown) operatively associated with the connector module 16. Alternatively, a rotary encoder (also not shown) mounted to the motor shaft or lead screw 24 may be used to derive information about the position of the connector module 16. In still another arrangement, motor control system 78 could sense the voltage and or current provided to motor 22 to derive information regarding the kinematic parameters of connector module 16. Travel limits (e.g., when the pins reach the ends of their respective slots) can be derived by detecting the increased current requirements of motor 22 when actuator 10 reaches the travel limits.

Motor control system 78 may also be configured to control the motor 22 based in part on the strain on actuator 10. In such a configuration, the actuator 10 may be provided with a load cell or strain gauge 80 capable of measuring the strain in the actuator. The load cell or strain gauge 80 may be operatively connected to motor control system 78 which may thereafter control the motor 22 based in part on the measured strain. The strain detected by load cell may also be used to determine the stress in the actuator 10, as would become apparent to persons having ordinary skill in the art.

In one embodiment, the motor control system 78 comprises a closed-loop motor control system that produces a pulse-width-modulated (PWM) signal for causing motor 22 to rotate in the desired direction and at the desired speed. However, because motor control systems suitable for controlling motor 22 are well-known in the art and could be readily provided by persons having ordinary skill in the art after having become familiar with the teachings provided herein, the particular motor control system 78 that may be utilized in one embodiment will not be described in further detail herein.

Actuator 10 may be operated as follows to apply a contractile and/or extensive forces to a load or object 36. As mentioned above, in most applications, actuator 10 will be operated primarily to provide contractile forces to closely simulate biological muscle contraction. As such, the load (e.g., moveable object 36) connected to actuator 10 will be biased in the extended position. That is, the load or object 36 will tend to return to its initial position once the contractile force applied by actuator 10 is removed. Alternatively, the actuator 10 may be operated to apply an extension force (i.e., in the direction of arrow 31) as well.

In an exemplary application wherein the actuator 10 is to be operated in a manner to simulate biological muscle contraction, the actuator 10 will be pre-loaded. That is, when the object 36 is located at some initial position, the elastic element 18 will be elongated slightly, and will apply a slight contractile force to the object 36.

Additional contractile force can be applied to the object 36 by operating control system 78 as necessary to move the actuator 10 in the contractile direction (i.e., in the direction of arrow 30). High speed rotation of motor 22 will result in the rapid contraction of actuator 10, whereas lower speed rotation of motor 22 will result in a lower contraction rate. More specifically, when operated in a contraction mode, motor 22 will rotate the lead screw 24 in a direction that will cause the nut 26 (FIGS. 3 and 4) to move in direction 30. The movement of nut 26 will cause the connector member 16 and free member 14 to move in direction 30 as well. As the connector member 16 moves in direction 30, it pulls on free member 14 via elastic element 18. Elastic element 18 extends or stretches until the force exerted on elastic element 18 equals the resistance offered by the object 36. Thereafter, moveable object 36 will move in direction 30.

In an embodiment wherein the elastic element 18 is non-linear, i.e., wherein the elastic element 18 comprises the trapezoidal configuration illustrated in FIGS. 2 and 3, the compliance of actuator 10 will decrease (i.e., become less compliant) with increased contraction forces. Conversely, the compliance of actuator 10 will increase (i.e., become more compliant) with decreased contraction forces. As discussed herein, the inverse relationship between compliance and contraction force is consistent with the titin model of biological muscle contraction.

Moreover, the compliance of the actuator 10 may be selected or "tuned" to a particular application by providing the elastic element with the appropriate shape and/or configuration. Alternatively, if the actuator 10 is provided with an adjustable elastic element 118, as illustrated in FIG. 5, then the compliance of actuator 10 can not only be easily tuned for a particular application (e.g., by operating the control system 127 to change the operating length 119 of elastic element 118), but can also be tuned or changed on-the-fly, i.e., when the actuator 10 is being operated. Thus, appropriate operation of the adjustable elastic element 118 can be used to cause actuator 10 to more closely simulate or mimic the dynamics of biological muscle contraction.

In addition to the operation of the actuator 10 in a contraction phase, described above, actuator 10 may also be operated in an extension phase. Operation in the extension phase may be conducted to allow the object 36 to return to the initial position, i.e., by reducing the contraction force below the return bias. Alternatively, operation in the extension phase may be conducted so as to cause actuator 10 to apply to object 10 an extension force, i.e., a force in the direction of arrow 31. Operation of actuator 10 in the extension phase may be accomplished by reversing the direction of motor 22. To the extent that elastic element 18 is stretched or elongated during the contraction phase, movement of the actuator 10 in the extension phase will be assisted by the energy stored in elastic element 18. That is, elastic element 18 will do work on drive system 20, thereby returning to the system energy stored in elastic element 18 during the contraction phase. If the elastic element 18 becomes fully relaxed, continued rotation of lead screw 24 will cause the connector module 16 to continue to move in direction of arrow 31, until pins 60 and 62 contact the ends of respective slots 56 and 58, at which point continued movement of connector module 16 will result in corresponding movement of free member 14 in the direction of arrow 31.

Figure 6:
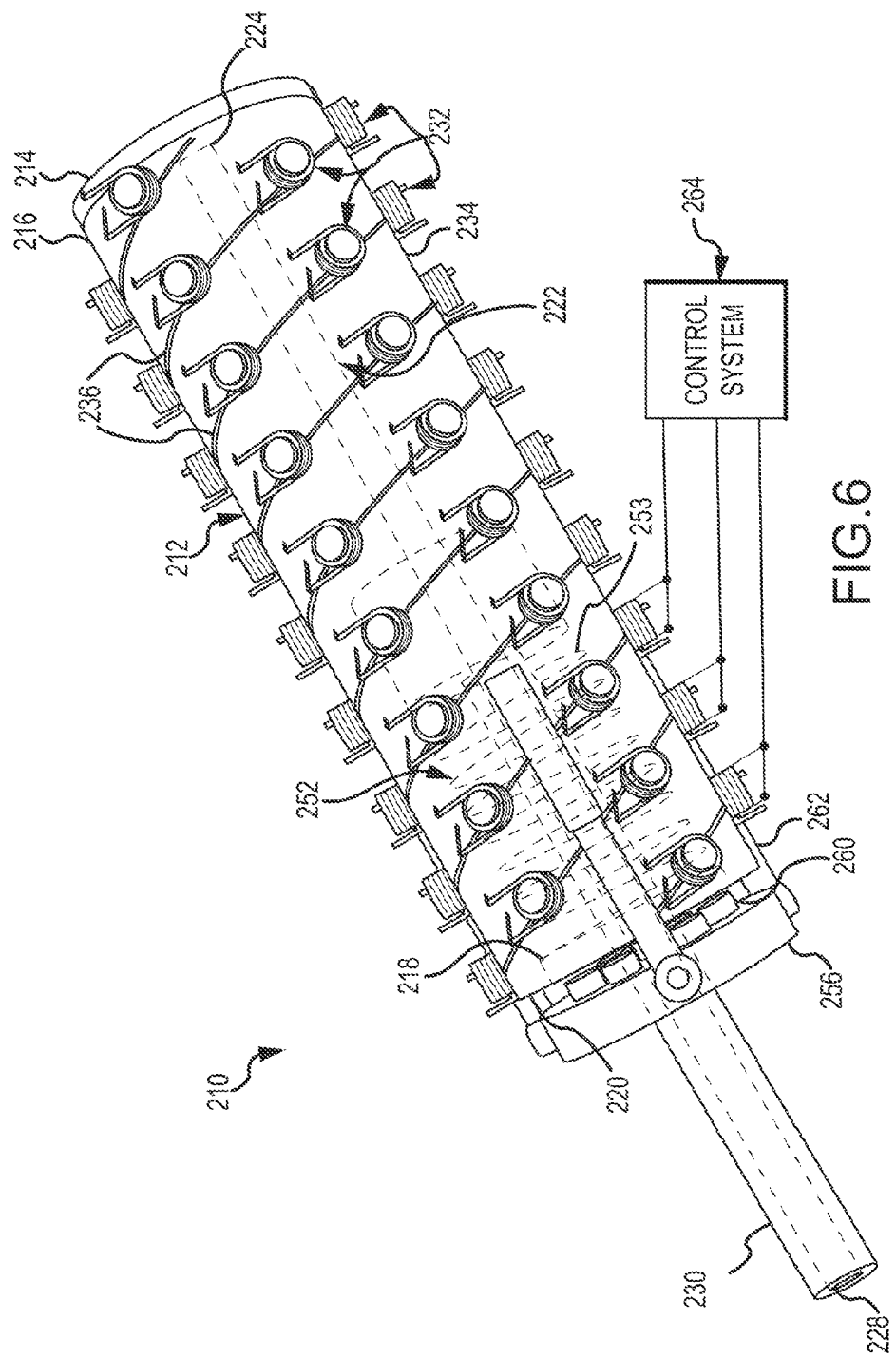
FIG. 6 is a perspective view of a second embodiment of an actuator showing the placement of external electromagnets along helical paths.
Figure 7:
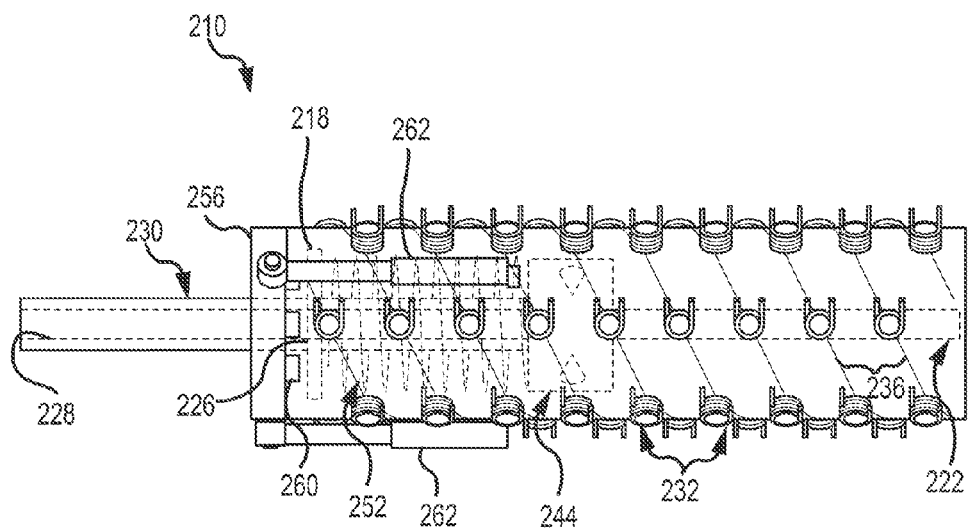
FIG. 7 is a side view in elevation of the actuator illustrated in FIG. 6.

Another embodiment 210 of an actuator is best seen in FIGS. 6-11 and may comprise a hollow cylindrical casing or housing 212 having a cap 214 at its fixed end 216 and a base 218 at its free end 220. Base 230 may also be provided with a central aperture or opening therein (not shown) sized to slidably receive a rotor shaft 230. A central guide member or rod 222 extends along the length of the cylindrical housing 212, i.e., between the fixed end 216 and the free end 220, as best seen in FIGS. 6 and 7. More specifically, distal end 224 of guide member or rod 222 may be attached to the cap 214, whereas proximal end 226 of guide rod 222 may be substantially supported within a central bore 228 of rotor shaft 230, as best seen in FIG. 7. Thus, in this embodiment 210, the fixed member is the housing 212, whereas the free member is the rotor shaft 230.

Figure 8:
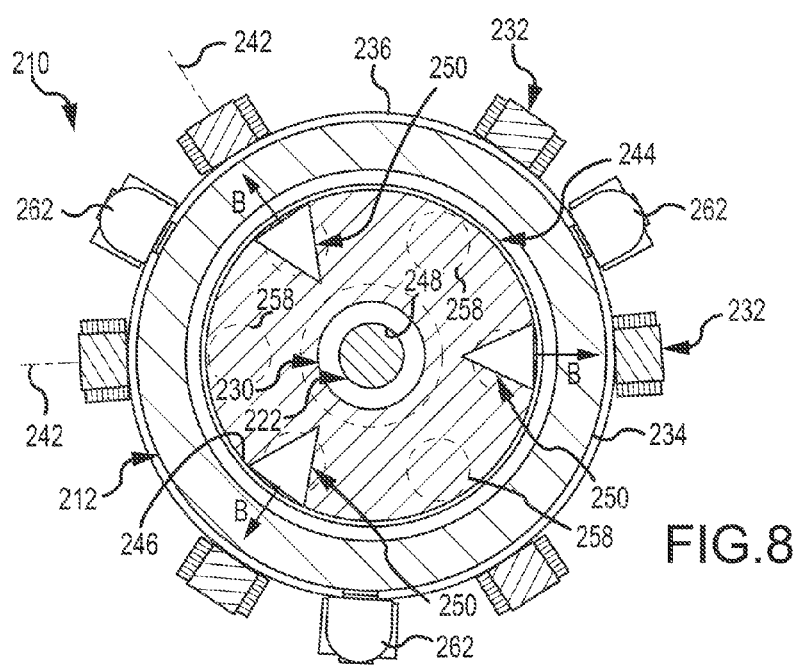
FIG. 8 is an end view of the actuator showing the arrangement of the rotor head magnets and external electromagnets.

Actuator 210 may also be provided with a plurality of electromagnets 232 mounted around the outer periphery 234 of cylindrical housing 212 along one or more helical paths or tracks 236. In the embodiment shown and described herein, the various electromagnets 232 are arranged around the outer periphery 234 of housing 212 along three (3) separate helical paths or tracks 236. Such a configuration allows the electromagnets 232 to be mounted at six positions or locations around the housing 212, as best seen in FIG. 8. Alternatively, the various electromagnets 232 may be mounted around housing 212 along a greater or lesser number of helical paths 236.

In the embodiment shown and described herein wherein the various electromagnets 232 are mounted along three separate helical paths 236, the various electromagnets 232 may be positioned around the outer periphery 234 of housing 212 at intervals of about 60 degrees, as best seen in FIG. 8. This arrangement is geometrically efficient and represents the fewest number of electromagnets 232 needed to generate magnetic fields capable of covering the largest possible rotor assembly 244, thereby improving the rotational momentum of the rotor assembly 244. The minimum number of electromagnets 232 required for each 360 degrees of helical track 236 is six (6). A larger number of electromagnets 232 per 360 degrees of helical track 236 could be used and may provide better rotational resolution (i.e. the shaft 230 could complete a rotation of 360 degrees in a larger number of discrete steps).

Figure 9:
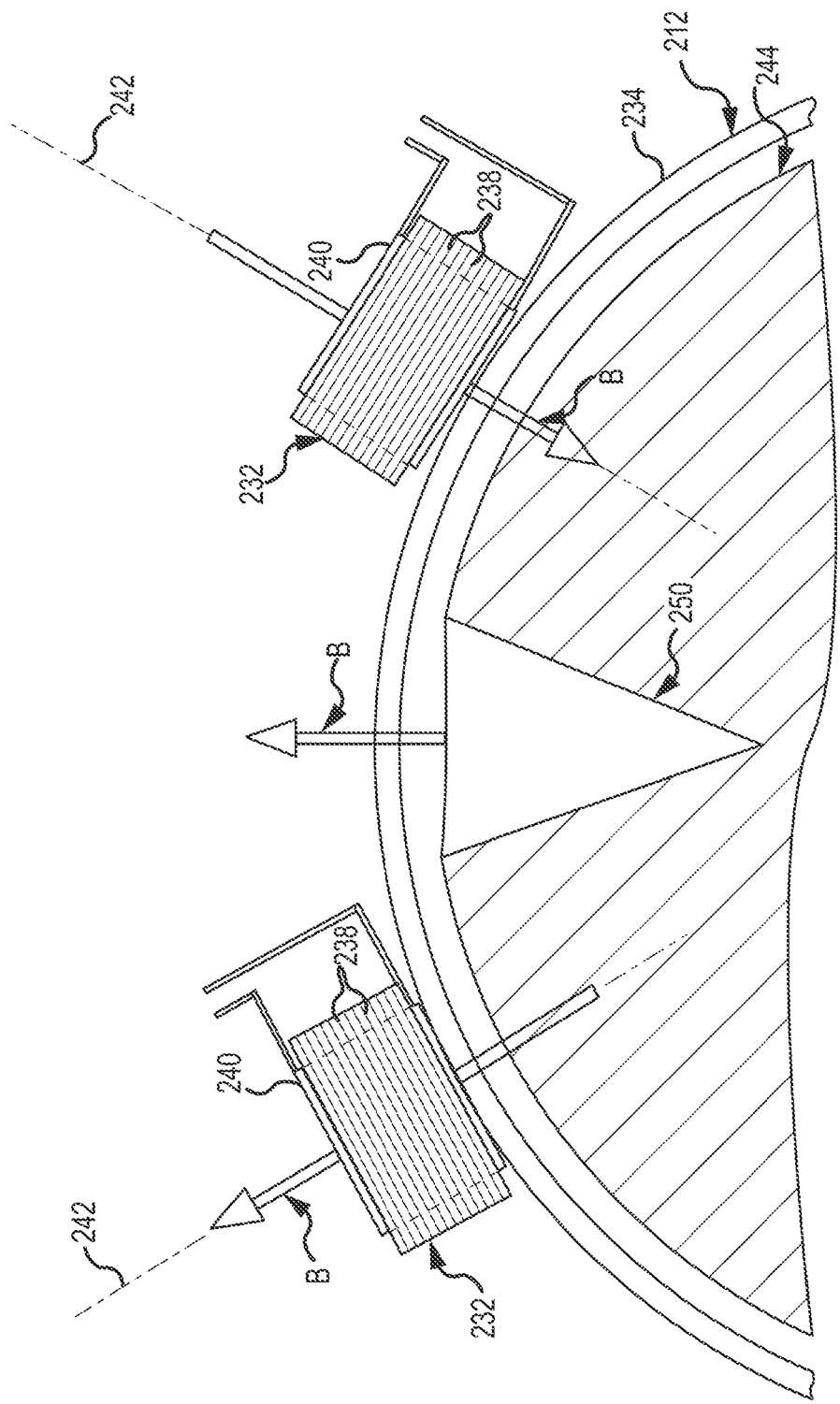
FIG. 9 is an enlarged end view of a portion of the rotor head showing the relative orientations of the magnetic fields of one rotor head magnet and a pair of external electromagnets.

Each electromagnet 232 may comprise a plurality of windings or coils 238 that are wrapped around a core 240. The various electromagnets 232 are oriented such that the axis 242 of each electromagnet 232 is generally perpendicular to the tangent of the curvature of the helical path 236, as best seen in FIG. 9. This arrangement allows the magnetic field vector B to point toward or away from the central guide member 222 of actuator 212, depending on the polarity of the voltage that is applied to the windings 238.

The various electromagnets 232 may be identical to one another, having the same number of windings 238, wound in the same direction, and around the same type of core 240. By way of example, core 240 may comprise a ferrite material. Alternatively, the core may comprise air. The windings or coils 238 may be a single layer or more preferably multiple layers of insulated wire.

Referring back now primarily to FIGS. 6-8, actuator 210 may also comprise a rotor assembly 244 having a head 246 that is sized to be slidably received by cylindrical housing 212. Head 246 is also provided with a central opening 248 (FIG. 8) therein sized to slidably receive the central guide member 222. The rotor shaft 230 is fixedly attached to head 246 and is generally aligned with the central opening 248 provided in head 246 so that the central opening 248 is generally aligned with the central bore 228 of rotor shaft 230. See also FIG. 7. Thus, the rotor head 246 and shaft 230 may slide along guide member 222, e.g., generally between the retracted and extended positions illustrated in FIGS. 11(a) and 11(c). The arrangement also supports the proximal end 226 of guide member 222, as best seen in FIG. 7.

The head 246 of rotor assembly 244 may also be provided with a plurality of magnets 250 that are mounted thereto at generally evenly spaced locations around the head 246, as best seen in FIG. 8. The various magnets 250 provided on the head 246 of rotor assembly 244 may all be oriented in generally the same direction, e.g., so that the magnetic field vectors B of each magnet 250 are oriented generally outwardly, as best seen in FIGS. 8 and 9. Alternatively, the various magnets 250 could be arranged so that their north poles face generally inwardly (i.e., so that the magnetic field vector B of each magnet 250 would point generally inwardly, toward the guide member 222).

Generally speaking, the relationship between the number of magnets 250 and the number of helical tracks 236 should be 1:1. That is, head 246 should be provided with the same number of magnets 250 as there are helical tracks 236. Alternatively, there may be a benefit to having multiple helical tracks 236 per magnet 250 if the number of electromagnets 232 per 360 degrees of helical track 236 differs from the number provided in the exemplary embodiment. Such an arrangement will function as a form of a transmission, in that it may be used to vary the angular velocity of the output shaft 230, but at the expense of torque. The combination of the electromagnets 232 and magnets 250 forms a drive means for moving the free member (i.e., rotor shaft 230) with respect to the fixed member (i.e., housing 212).

Figure 10:
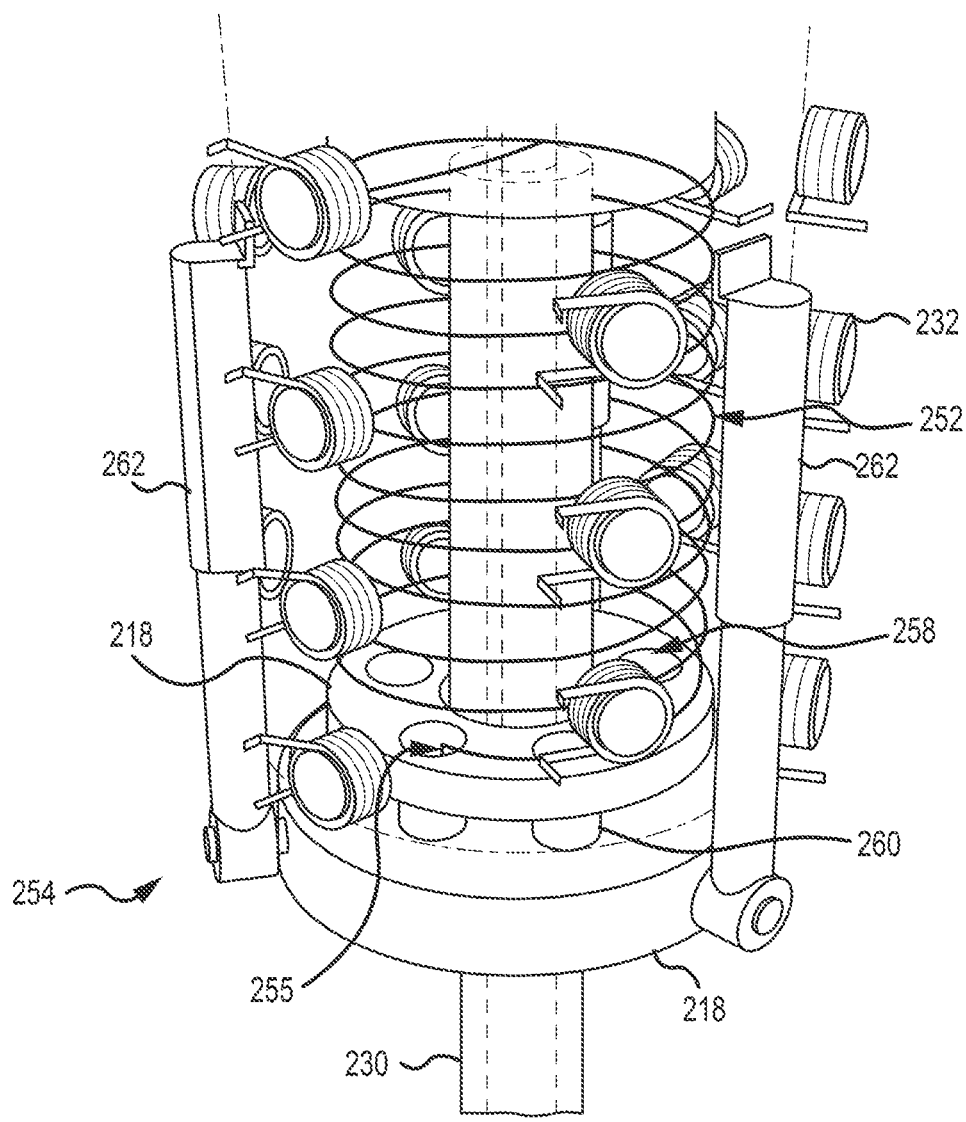
FIG. 10 is an enlarged perspective view of the actuator illustrated in FIG. 6 more clearly showing the catch for enabling and disenabling spring rotation.

The actuator 210 may also be provided with an elastic element or spring 252 positioned between the head 246 of rotor assembly 244 and the base 218, as best seen in FIGS. 6, 7, and 10. One end 253 of spring 252 may be fixedly attached to the head 246 of rotor assembly 244, whereas the other end 255 of spring 252 is configured to operatively engage base 218 of actuator 210. A catch assembly 254 may be used to cause the end 255 of spring 252 to engage and disengage from the base 218. More specifically, in the embodiment shown and described herein, the base 218 of actuator 210 may be provided with one or more holes 258 therein that are sized to engage with the end 255 of spring 252. A disk 256 having one or more pins 260 provided therein may be mounted to the housing 12, e.g., by one or more actuators 262 in the manner best seen in FIGS. 6, 7, and 10. The actuators 262 may cause the disk 256 to move toward and away from base 218. When the disk 256 is moved toward base 218, the pins 260 engage the corresponding holes 258 in base 218, ultimately pushing end 255 of spring 252 out of the hole 258, thereby disengaging spring 252 from base 218. Because the pins 260 are flush with the surface of base 218, the end 255 of spring 252 will slide around the base 218 as the head 246 of rotor assembly 244 turns without becoming re-engaged with base 218. However, when the disk 256 is moved away from the base 218, the pins 260 disengage from holes 258, allowing the end 255 of spring 252 to re-engage with one of the holes 258.

The spring 252 thus allows the actuator 210 to store energy in two different manners. First, spring 252 can be compressed between the head 246 and the base 218, thus storing energy. Second, spring can also store energy by being wound up as the head 246 of rotor assembly 244 turns in the manner described herein. Because spring 252 is attached to head 246, the spring 252 is able to store energy both by compression and by winding.

Actuator 210 may also be provided with one or more sensors (not shown) to detect the position of the rotor assembly 244 with respect to the housing 212. It is generally preferred, but not required, that the sensor comprise a non-contact type of sensor to decrease the overall friction load of the system. Exemplary non-contact sensors include optical sensors and magnetic feedback sensors. Optical sensors may require a slotted disk to be affixed to the rotor head 246 or rotor shaft 230 such that light traveling between a source and detector is interrupted as the rotor head 246 moves within housing 212. The interruptions are counted by a processing unit and the rotational speed and position are calculated.

Alternatively, the electromagnets 232 themselves may be used as non-contact sensors. For example, by multiplexing the electromagnet's 232 purpose as an attractive, or repulsive magnet, and as a sensor at a very high rate, the electromagnets 232 can be used to determine the location of the magnets 250 in the rotor head 246. That is, the movement of the magnets 250 past the coils 238 in each electromagnet 232 will cause a measurable back-current to be generated in the coil 238.

Actuator 210 may also comprise a control system 264 operatively connected to each of the electromagnets 232. Control system 264 is used to energize the various electromagnets 232 to cause the rotor assembly to both rotate and move from end-to-end, generally along a helical path in the manner described below.

The control system 264 may comprise any of a wide range of hardware and/or software elements (not shown) suitable for applying an electric current to each of the various electromagnets 232.

Referring now primarily to FIG. 9, the magnetic fields B produced by each electromagnet 232 resembles a dipole and the strength of the field decreases as a function of the inverse of the cube of the distance from the electromagnet 232. This magnetic field B can turn on, off, grow, shrink, and reverse depending on the control of the current energizing the electromagnet 232. In the example embodiment illustrated in FIG. 9, the right electromagnet 232 is energized such that the net magnetic vector B (shown by the arrow) is pointing towards that of the magnet 250 in the rotor head 246. As such, these magnets are opposing and therefore repulsive. This enhances the rotation of the rotor head 246 that is spinning under its own momentum. The magnetic field vector B of magnet 250 is pointing away from the left electromagnet 232, as this electromagnet 232 is passing current that is opposite to that in the right electromagnet 232. The magnet 250 on rotor head 246 is therefore attracted to this electromagnet 232. Thus the rotor 246 would move toward the left hand electromagnet 232 and generate torque.

An exemplary control schedule or methodology for applying electric current to each of the electromagnets 232 is as follows. If one numbers the electromagnets 232 along each helical path 236 from 1 at the bottom to N at the top (the maximum number of electromagnets 232 is not fixed as a longer actuator 210 would require more electromagnets 232), then to compress the spring 252 maximally and extend the rotor shaft or sleeve 230 to its longest length, one would energize the three #1 electromagnets 232 so that they attract the magnets 250 in the rotor head 246. Energizing the three #2 electromagnets 232 to attract the magnets 250 while reversing the current through the #1 electromagnets 232 would cause the rotor head 246 to be repulsed from the #1 electromagnets 232 and move toward the #2 electromagnets. As the rotor head 246 gains momentum, activating #3 electromagnets 232 causes the rotor 246 to move to an intermediate position between electromagnets #2 and #3. Reversing the current in the #2 electromagnets causes them to repel the rotor head magnets 250. The rotor head 246 then rotates towards the #3 electromagnets 232. Thus, to continue rotating/retracting the shaft 230 a staggered progression of electromagnet energizations in which the electromagnet 232 is off, then turning on (attracting), then reversing the current (repelling), then turning off will allow control of the position of the rotor assembly 244, thus output shaft or sleeve 230.

This type of control of the electromagnets 232 is possible by using a series of transistors and pulse width controller with programming similar to that of a conventional stepper motor controller. The duty cycle of the electromagnets 232 (i.e. the length of energization time) in this cyclical progression depends on the strength of the electromagnets 232, the required speed of shaft rotation, the strength of the spring 252, the momentum of the rotor head 246 and the physical dimensions of the actuator 210.

To use the electromagnets 232 to sense the position of the rotor head 246, the control system 264 would have to detect or measure the voltage induced in the electromagnets 232 as the magnets 250 in the head 246 pass nearby. Such a voltage measurement can be made extremely quickly so that the momentum of the rotor head 246 keeps the shaft 230 moving, as the electromagnet 232 is not energized during the sensing operation. A computer (not shown) with an analog to digital conversion/data acquisition device or a programmable integrated circuit with enough input/output channels is capable of providing this control.

The rotor assembly 244 is capable of sliding along the guide member 222 for most of its length. The rotor assembly 244 can move along the guide member 222 by sequential activation of the electromagnets 232 in the manner described herein. In addition, the rotor assembly 244 can also move along the guide member 222 under the influence of energy returned by the spring.

Figures 11A, 11B, 11C:
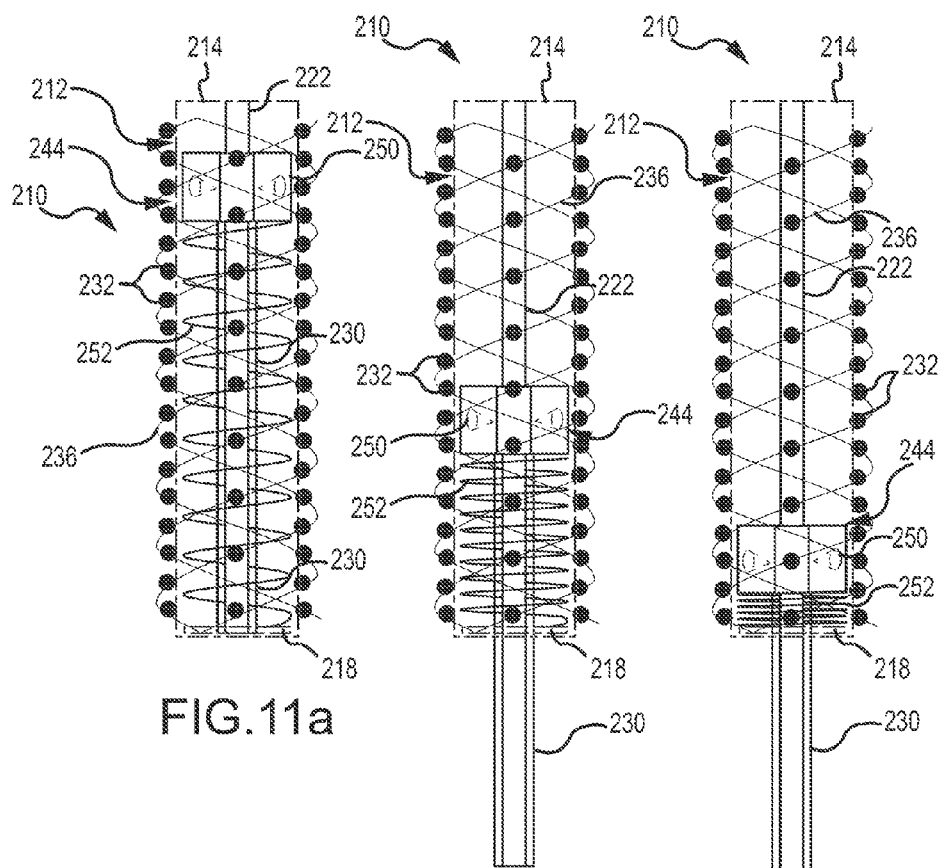
FIGS. 11 (*a-c*) show the actuator in three different positions, a contracted position, an intermediate position, and an extended position, respectively.

Referring now primarily to FIG. 11(a-c), in the neutral position (FIG. 11b), the spring 252 is at its resting length and exerts no force on the rotor head 246. Sequentially energizing the electromagnets 232 causes the magnets 250, thus rotor head 246 to rotate and translate along a helical path described by their arrangement. Both rotation and translation of the rotor head 246 result in storage of elastic potential energy in the spring 252. See FIG. 11a. Translation of the rotor head 246 stretches the spring 252, while rotation of the rotor head 246 will wind the spring 252 around the rotor shaft 230 when the spring 252 is fixed to (i.e., engaged with) the base 218. At maximum spring extension, the free end of shaft 230 is in the retracted position illustrated in FIG. 11a.

The spring 252 can be compressed (FIG. 11c) by applying a tensile force at the end of the shaft 230, or by reversing the direction of sequential activation of the electromagnets 232. Either a force applied at the end of the shaft 230 or the force of attraction between the electromagnets 232 and the magnets 250, or both, can prevent the stretched spring 252 from recoiling to its resting position. Thus, not only can the actuator 210 do work on the spring 252, but spring 252 can do work on actuator 210.

High thermodynamic efficiency results from the fact that stored elastic potential energy is used to accelerate and decelerate the rotor assembly 244 instead of electricity.

Intrinsic stability arises because the rotor assembly 244 is free to move within the cylinder housing 212. Oscillations of the spring 252 reduce transmission of applied forces to the fixed end 214 of the actuator 210. Electromagnetic forces will damp the oscillations of the spring 252. Changes in the applied force will automatically result in changes in the position of the rotor assembly 244 (and therefore changes in the energy stored in the spring 252). The spring 252 will become stiffer (i.e., actuator 210 will become less compliant) when the compressive force increases. Actuator 210 will become more compliant when the compressive force decreases. The actuator 210 therefor exhibits viscoelastic properties.

The actuators described above may be designed to mechanically mimic muscle behavior including muscle behavior based on winding filament properties of titin. Actuator control systems will now be discussed which are used to mechanically mimic muscle properties through the use of mechanical and software elements, including using one or more control algorithms implemented through software that are based on a winding filament theory (WFT) or model for titin. Such an actuator control system may include any element(s), detail(s), configuration(s), design(s), method(s) and so forth, disclosed in any of the following references, each of which is entirely incorporated herein by reference: A. Hessel, U. Tahir, J. Petak, R. LeMoyne, Z. Han, J. Tester, K. Nishikawa, "A Neuromuscular Algorithm for a Powered Foot-Angle Prosthesis Shows Robust Control of Level Walking and Stair Ascent," abstract submitted for 7th International Symposium on Adaptive Motion of Animals and Machines (AMAM 2015), June 21-2015, Cambridge, Mass., submitted herewith as Appendix A; A. L. Hessel, U. Tahir, J. Petak, R. C. LeMoyne, Z. Han, J. Tester, K. C. Nishikawa, "A Neuromuscular Algorithm for a Powered Foot-Ankle Prosthesis Shows Robust Control of Level Walking and Stair Ascent," abstract submitted for a July 2015 conference, submitted herewith as Appendix B; J. Tester, S. H. Yeo, D. Pai, K. Nishikawa, "A new muscle model with implications for actuation and control," Proceedings of the 7th Annual Dynamic Walking Conference, 2012, Pensacola Beach, Fla., submitted herewith as Appendix C; Jeremy L. Petak, "Performance testing of a musculoskeletal model controller for a robotic prosthesis," M. S. Thesis, Northern Arizona University, Thesis No. 1571866 published 2014 in Ann Arbor, Mich. by ProQuest UMI Dissertations Publishing (Document ID 1648961412, ISBN 9781321449303); J. Petak, N. Heckathorn, R. LeMoyne, J. Dyer, S. H. Yeo, D. Pai, J. Tester, K. Nishikawa, "Windng filament muscle model for musculo-skeltal simulations," published 2013, submitted herewith as Appendix D; R. LeMoyne, J. Petak, J. Tester, K. Nishikawa, "Simulation of a computational winding filament model with an exponential spring to represent titin," 36th Annual International IEEE Conference of Engineering in Medicine and Biology Society (EMBC), pp. 836-839, Aug. 26-30 2014, Chicago, Ill., submitted herewith as Appendix E; A. L. Hessel, J. Petak, R. C. LeMoyne, J. Tester, K. C. Nishikawa, "Emulating Human Walking with a Powered Ankle-Foot Prosthesis, Driven by a Neuromuscular Based Control Algorithm," poster used at a 2015 presentation, submitted herewith as Appendix F, and; K. C. Nishikawa, J. A. Monroy, T. E. Uyeno, S. H. Yeo, D. K. Pai, S. L. Lindstedt, "Is titin a 'winding filament'? A new twist on muscle contraction," Proc. R. Soc. B. (2012) 279, pp. 981-990.

Figure 12:
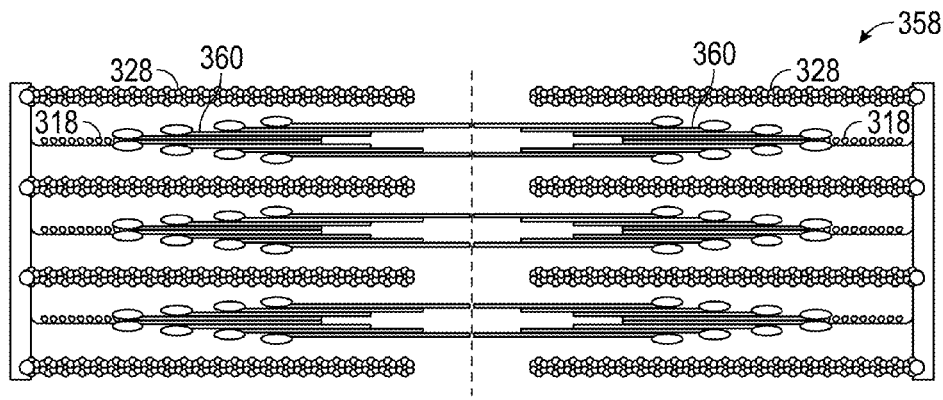
FIG. 12 is a front view of a sarcomere.
Figure 13:
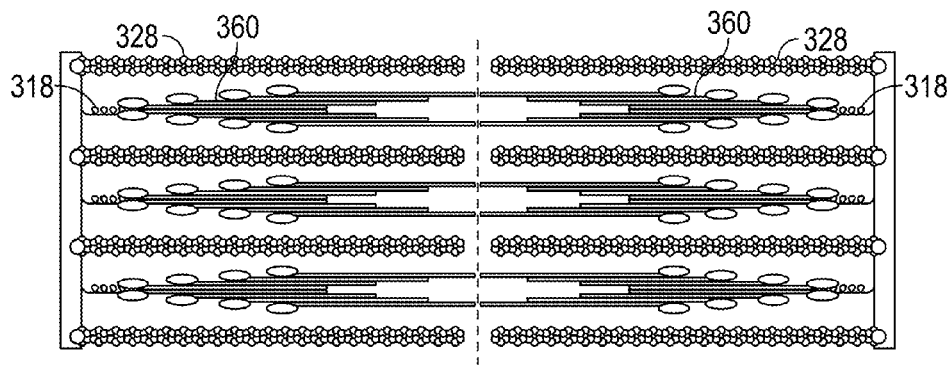
FIG. 13 is a front view of the sarcomere of FIG. 1 in a contracted state.

Referring now to FIGS. 12-23, various aspects of models used to model muscle actuation will be described. Details of these models are described in greater detail in the above cited references which have been incorporated by reference, and reference is made to them to provide further details and understanding of the related models. FIG. 12 shows a sarcomere 358 in an uncompressed state. The sarcomere includes a number of myosin filaments (thick filaments) 360 that interact with actin filaments (thin filaments) 328. A titin filament 318 attaches each myosin filament to the z-disk. FIG. 13 shows a sarcomere 358 with the same elements but in a compressed state. Applicants credit David Richfield, "Medical gallery of David Richfield 2014," Wikiversity Journal of Medicine 1(2) as the basis for FIGS. 12-13.

Figure 14:
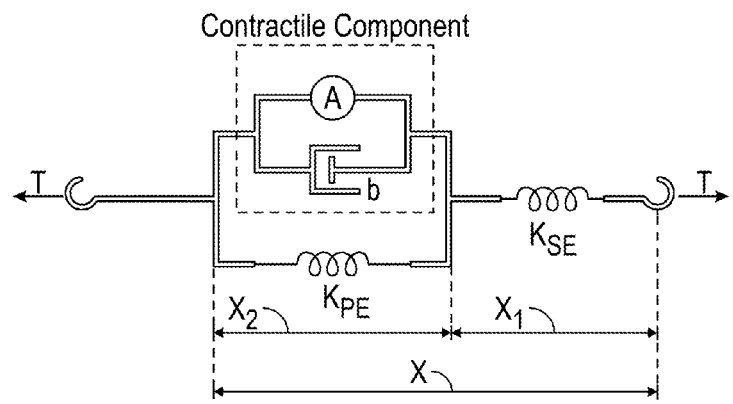
FIG. 14 is a diagram showing elements of a sliding filament (Hill) muscle model.

The interaction of actin and myosin in muscle has been modeled using a "sliding filament" theory (Hill model) in the past, but this model was created before titin was discovered. Accordingly, it did not take into account any effects of titin in muscle actuation. FIG. 14 shows various components of the traditional sliding filament model of muscle actuation. A contractile component having a contractile element A and a damping element b is in parallel with a spring, and both of these are in series with a series spring having a spring constant $K_{PE}$. A series spring having spring constant $K_{SE}$ is also included. Tension is applied to the ends at the T locations, and the length of the series spring $X_1$, the length of the parallel contractile and spring element $X_2$, and the total length X are represented.

Figure 15:
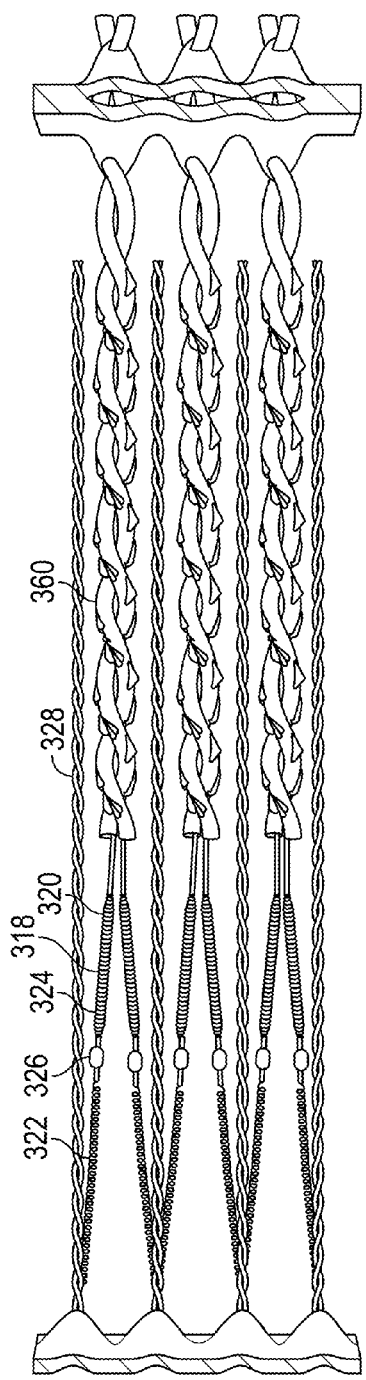
FIG. 15 is a front view of a portion of a sarcomere.

The traditional sliding filament model represented in FIG. 14 does not take into account the effect of titin during muscle actuation. A theory of titin's role in muscle actuation is described in detail in the references cited above that are incorporated by reference, but a brief overview will be given here. Referring to FIG. 15, a half sarcomere is shown with myosin filaments 360 and actin filaments 328. Titin filaments 318 are also shown, which are modeled as winding filaments 320, which will be described hereafter. Each titin filament includes a first section 322 having first elastic properties (which may be represented by a first spring constant and/or other elements) and a second section 324 having second elastic properties (which may be represented by a second spring constant and/or other elements). Each titin filament further includes an N2A region 326.

Figure 16:
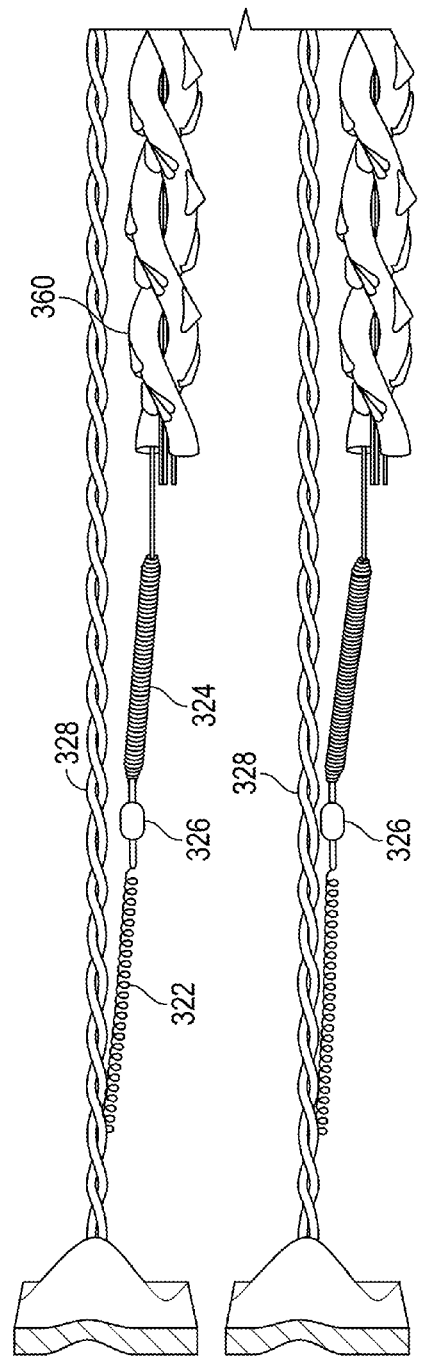
FIG. 16 is a front view of a portion of the sarcomere of FIG. 4 with an N2A region of a titin filament binding to an actin thin filament.

FIG. 16 represents a theoretical binding process by which a titin filament binds to a neighboring actin filament. It is hypothesized that during an influx of $Ca^{2+}$ in skeletal muscle, the N2A region of titin binds with the neighboring actin filament. As can be imagined, if the first section 322 is more elastic than the second section 324 (which second section is a PEVK region), as is theorized, then upon binding of the N2A region with the actin filament the overall elasticity of the titin filament is reduced, which would provide greater resistance to a stretching of the titin filament.

Figure 17:
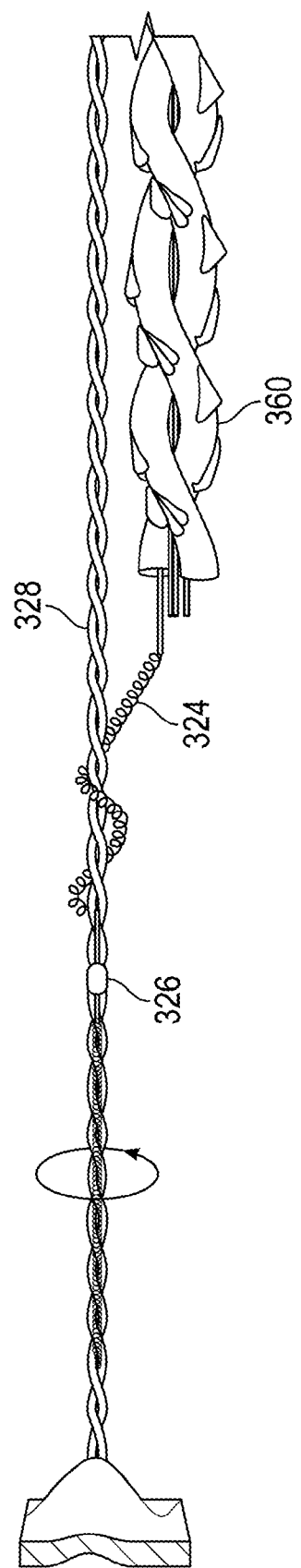
FIG. 17 is a front view of a portion of the sarcomere of FIG. 4 with a portion of the titin filament wound around the actin thin filament.
Figure 18:
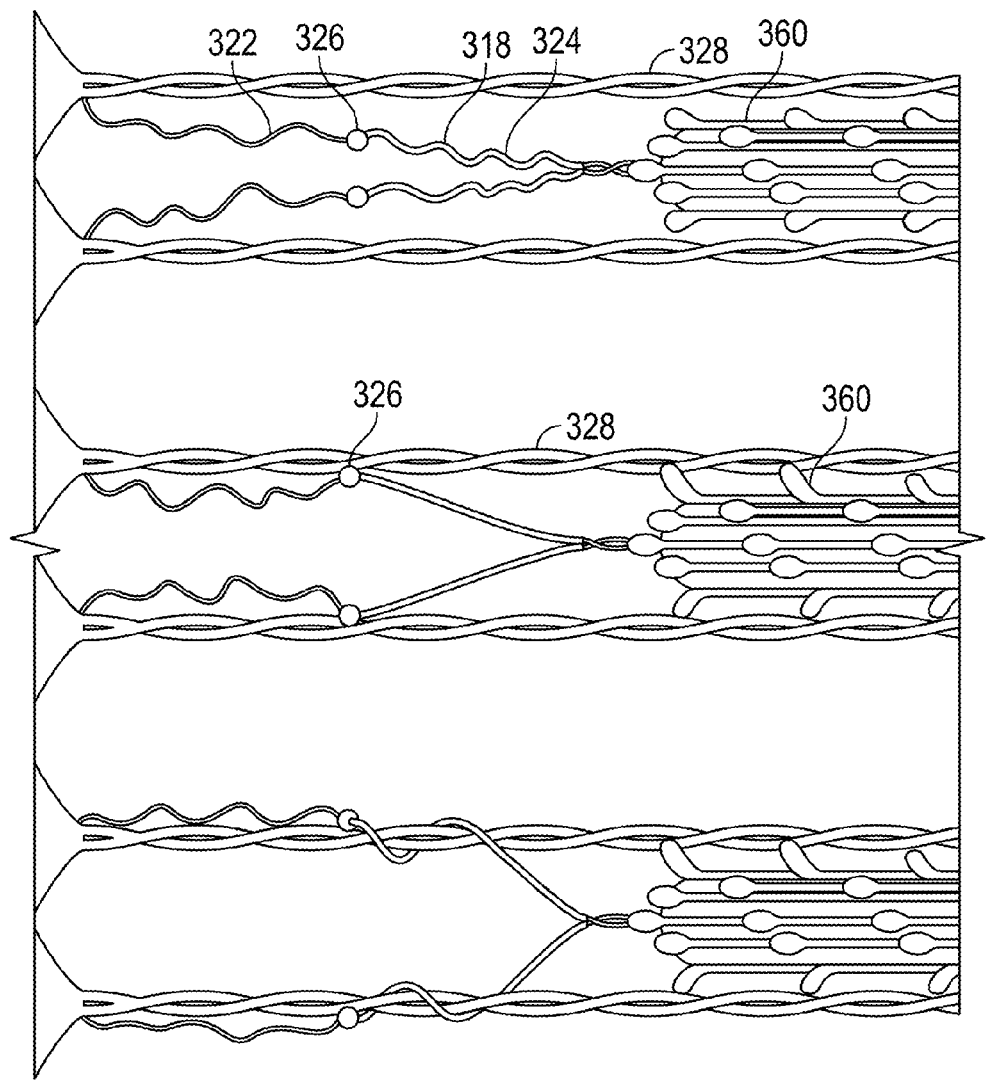
FIG. 18 is a front view of a portion of a sarcomere showing an N2A region of a titin filament binding to an actin thin filament and the titin filament wound around the actin thin filament.

FIGS. 17-18 show another hypothesized interaction of the titin filament with the neighboring actin filament. Upon further stretching of the titin filament it is theorized that the myosin filament cross-bridges twist the actin filament to which the titin filament is attached (through the N2A region) so that the second section 324 of the titin filament is wound up around the actin filament. Naturally, as such a process occurs the free length (i.e., the length not wound around the actin filament) will be reduced, and the angle where the second section of the titin filament meets the myosin filament will be altered, which may affect the properties of the sarcomere during muscle actuation.

Thus, the winding filament theory (WFT) includes the concepts that an N2A region of titin binds to actin thin filaments upon Ca' influx in skeletal muscle, and that PEVK titin winds on the actin thin filaments during force development because the myosin cross-bridges not only translate but also rotate the actin thin filaments.

A mathematical model which includes representations of the stretching of titin, binding of titin to actin, and winding of titin around actin may be used to describe forces during muscle actuation. Such characteristics may explain mechanisms for storage and later release of energy between contraction and stretch stages of muscle actuation.

Modeling of muscles may be based on specific muscles or muscle groups within the body of a human or other animal. By non-limiting example, referring to FIG. 19, elements representative of muscles connecting a leg and foot of a human are shown. The central mostly vertical line represents a leg (or one or more bones within the leg) and the horizontal line at the bottom represents the foot. Two muscle tendon units 344 are shown, one is a virtual anterior muscle 346, which is modeled after the tibialis anterior and is attached to the leg (or bone of the leg using a tendon) at a first attachment location 348 and to the foot (or bone of the foot using a tendon) at a second attachment location 350. A virtual posterior muscle 352 is modeled after a combination of the soleus and gastrocnemius muscles and is attached to the leg (or bone of the leg using a tendon) at a first attachment location 354 and to the foot (or bone of the foot/heel using a tendon) at a second attachment location 356.

The length of the virtual anterior muscle, from its first attachment point to its second attachment point, is represented by Lm_A, which value naturally changes as the muscle contracts and stretches. The length of the virtual posterior muscle, from its first attachment point to its second attachment point, is represented by Lm_P and also changes as the muscle contracts and stretches. At the second attachment location 350 the virtual anterior muscle exhibits a force on the foot, represented by the foot moment arm FMA_A. At the second attachment location 356 the virtual posterior muscle exhibits a force on the foot as well, represented by the foot moment arm FMA_P. These forces/torques combine for a resultant torque at the axle, which governs angle θ. The virtual anterior muscle forms an angle α with the foot and the virtual posterior muscle creates an angle β with the foot. Shank attachment lengths SAL_A and SAL_P may be varied, and are described in greater detail in the references cited above and incorporated by reference.

The simplified representation of a leg and foot, and an ankle joint, is just one representative example of a model configured to determine forces, angles, torques, and the like, of a joint. Other joints could be modeled in a similar manner, including a knee joint, and ankle joint, a shoulder joint, and so forth.

A mathematical model representing muscle actuation may include one or more values representing attachment parameters for the virtual muscles (for instance where the first and second attachment points are located for each virtual muscle) as well as activation levels (for instance whether the muscle is contracting/stretching at 10%, 20%, 50%, and so forth of maximum capacity).

Figure 19:
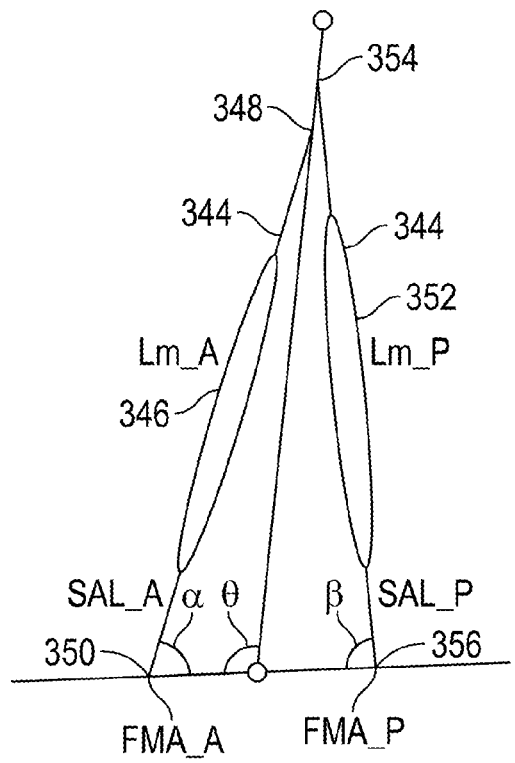
FIG. 19 is a diagram of a plurality of muscle tendon units (MTUs) used to model muscles coupled with a leg and a foot.

Referring now to the specific model of an ankle joint shown in FIG. 19, the force that each muscle tendon unit (MTU) 344 exhibits on the foot, depicted as FMA_A and FMA_P, may be calculated using a model to determine muscular force that is based on, or includes, the various properties of titin (stretching, N2A binding, and filament winding, as have been described above). By non-limiting example, a diagram of various elements of such a model is given in FIG. 20, where a contractile element 330 (CE) having a viscous damping element 332 with a damping rate $C_{ce}$ is in parallel with a spring (titin spring) 334 and, at the same time, is in series with the titin spring through a pulley 338. The damping rate may in implementations be bi-directional. The damping rate may also be related to a muscle activation level (for example a muscle may be activated between 0-100% of a maximum activation level and this percentage may affect the damping rate). In implementations the contractile element 330 represents myosin cross-bridges, the pulley represents actin thin filaments, and the titin spring represents titin.

The pulley 338 may rotate in either rotational direction and is centered about an axle 342. The pulley may also translate left and right (i.e., the axle is not fixed with respect to the horizontal direction). A second spring (series spring) 340 is attached to the axle 342 and represents one or more tendons attached to bone, whereas the other elements (contractile element, pulley, titin spring) are intended to model the interactions of actin, myosin, and titin during muscle actuation, as indicated above. The contractile element may represent a motor when the model is used to build a mechanical replica of muscle actuation. As can be understood, the motor/contractile element may extend/shorten the titin spring and forces that move the pulley may also extend or shorten the titin spring.

A clutch may be included on the axle to selectively prevent its rotation (which may model the binding of the N2A region of titin to actin), which would prevent the rotation of the pulley but would not prevent translation of the pulley in either horizontal direction based on stretching or contraction of the series spring and/or the combination of the titin spring and contractile element. The clutch would eliminate rotational force balance between the contractile element and titin spring. While the clutch is engaged the horizontal displacement of the contractile element and the titin spring would be equal and the titin spring would store more energy. The inclusion of a clutch may be used to model a force enhancement phenomenon, which may increase a muscle model's capacity to model stored energy during movement and which, when implemented in a control algorithm and related actuator control system, may reduce work of an actuator.

Figure 20:
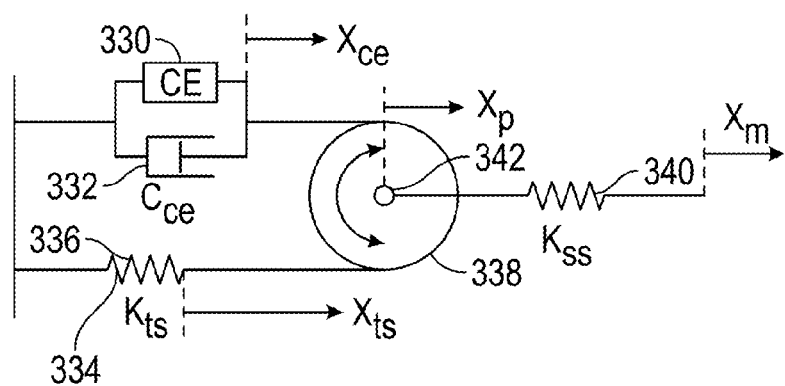
FIG. 20 is a diagram of elements of a model used to calculate force of a muscle tendon unit based on a winding filament theory (WFT) of titin.

In implementations the pulley may be modeled as a winding ratchet which, in the model shown in FIG. 20, itself resists rotation in the clockwise direction but generally does not resist rotation in the counterclockwise direction. As shown in the drawings, the titin spring is simultaneously in parallel with the contractile element and, through the pulley, in series with the contractile element.

Referring still to FIG. 20, changes in length of the contractile element/viscous damping element, titin spring, pulley axle, and the entire muscle tendon unit (MTU) are represented by $X_{ce}$, $X_{ts}$, $X_p$, and $X_m$, respectively. Spring constants of the titin spring and series spring are represented by $K_{ts}$ and $K_{ss}$, respectively.

The model shown in FIG. 20 may thus be used to calculate the force exhibited by a muscle tendon unit. For example, to calculate net torque on the ankle joint represented in FIG. 19, a mathematical model may include a first instance of all of the elements of FIG. 20 to represent the virtual anterior muscle and may further include a second instance of all of the elements of FIG. 20 to represent the virtual posterior muscle. Using such modeling/calculations, the overall torque at the ankle joint may be calculated. A control algorithm may thus include a mathematical representation of a contractile element, a viscous damping element in parallel with the contractile element, and a spring in series with the contractile element through a pulley and simultaneously in parallel with the contractile element to determine how to control a joint.

Figure 21:
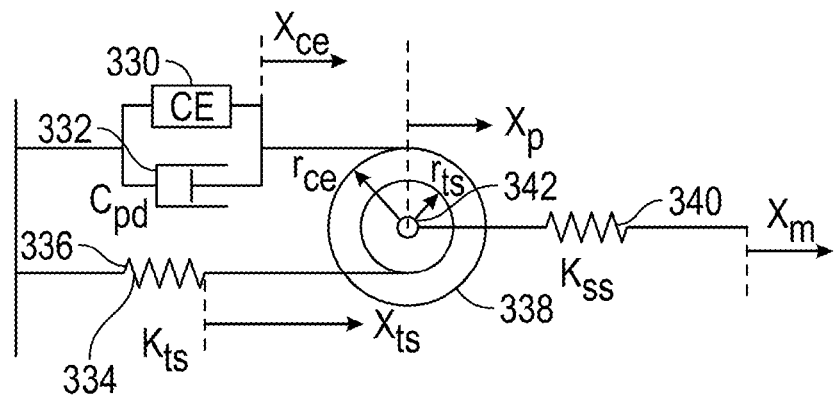
FIG. 21 is a diagram of elements of a model used to calculate force of a muscle tendon unit based on a winding filament theory (WFT) of titin.

In implementations the titin spring 334 may be a nonlinear spring (or in other words may have a nonlinear spring constant) such as an exponential spring 336 (with an exponential spring constant). An exponential spring may better match or represent the elastic properties of titin. Referring now to FIG. 21, in implementations the titin spring and contractile element/viscous damping element are modeled as acting on the pulley at different radii. In the example shown in FIG. 21 the contractile element is shown as acting on the pulley at the radius $r_{ce}$ while the titin spring is shown as acting on the pulley at the radius $r_{ts}$. The damping coefficient of the viscous damping element 332 of FIG. 21 is represented as $C_{pd}$.

Figure 22:
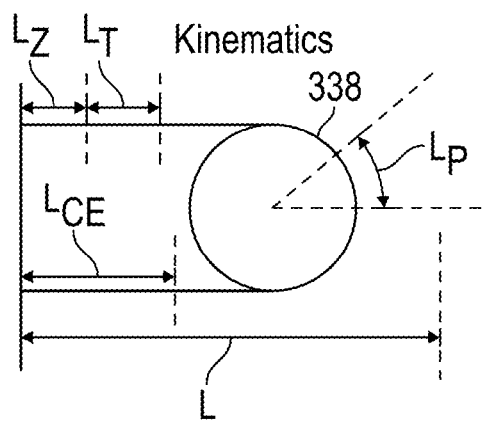
FIG. 22 is a close-up view of a pulley of the model of FIG. 9 illustrating kinematic elements.
Figure 23:
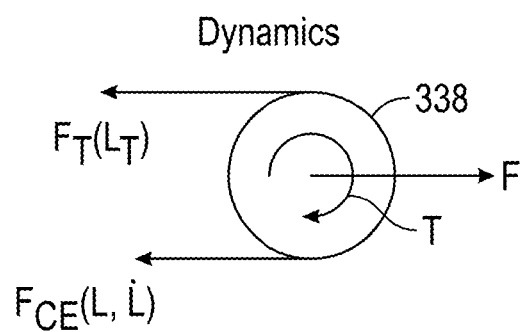
FIG. 23 is a close-up view of a pulley of the model of FIG. 9 illustrating dynamic elements.

FIG. 22 represents various kinematics of the system(s) represented by FIGS. 20-21. In FIG. 22 the subscripts Z, T, CE and P refer to the z-disk, the titin spring, the contractile element, and the pulley, respectively. The following equations may be used to model the kinematics of the pulley system: $2L = (L_T + L_Z(F_{CE}(L, \dot{L}))) + L_{CE} + \text{Constant}$, and; $L_P = L_{CE} - L + \text{Constant}$. FIG. 23 represents various dynamics of the system represented by FIGS. 20-21. The subscripts have the same meaning as in FIG. 22. The following equations may be used to model the dynamics of the pulley system: $F_T + F_{CE} = F$, and; $F_{CE} + T = F_T$. These elements and examples are described more fully in the cited references that have been incorporated by reference above.

Using the above models and relationships defined for various elements representing muscle sub-parts, such as titin, actin, myosin, tendons, and the like, a control algorithm may be formulated to control the torque on a joint according to one or more inputs. By non-limiting example, using an ankle joint as a representative example, a control algorithm may be designed to, based upon one or more external inputs, apply a torque on a motorized ankle joint in a manner similar to that which would be done by muscles acting on an intact ankle of a person. A similar modeling process can be used to created control algorithms for other muscle joints of a person or animal.

During ambulation, for example, various states may be present, such as: a standing state, a controlled plantar flexion state, a controlled dorsiflexion state, a powered plantar flexion state, an early swing state, and a late swing state. These six states are described in greater detail in the references above which are incorporated herein by reference. In implementations these states could be simplified to include fewer states or they could be expanded to include more states. The states could be sensed by one or more sensors which could sense, for example: an angle of rotation of an ankle joint; a velocity of rotation of an ankle joint; a direction of rotation of an ankle joint; a variety of forces acting on a foot and/or leg member as measured by pressure sensors on the foot itself and/or pressure sensors or strain gauges or the like in a diamond (or similar) connector at a distal end of a prosthetic; and so forth. Using such sensed data, a system may be designed to determine one of a finite number of states that an ankle joint is in and, according to the sensed state, apply an appropriate torque to the ankle joint using the control algorithm.

Figure 24:
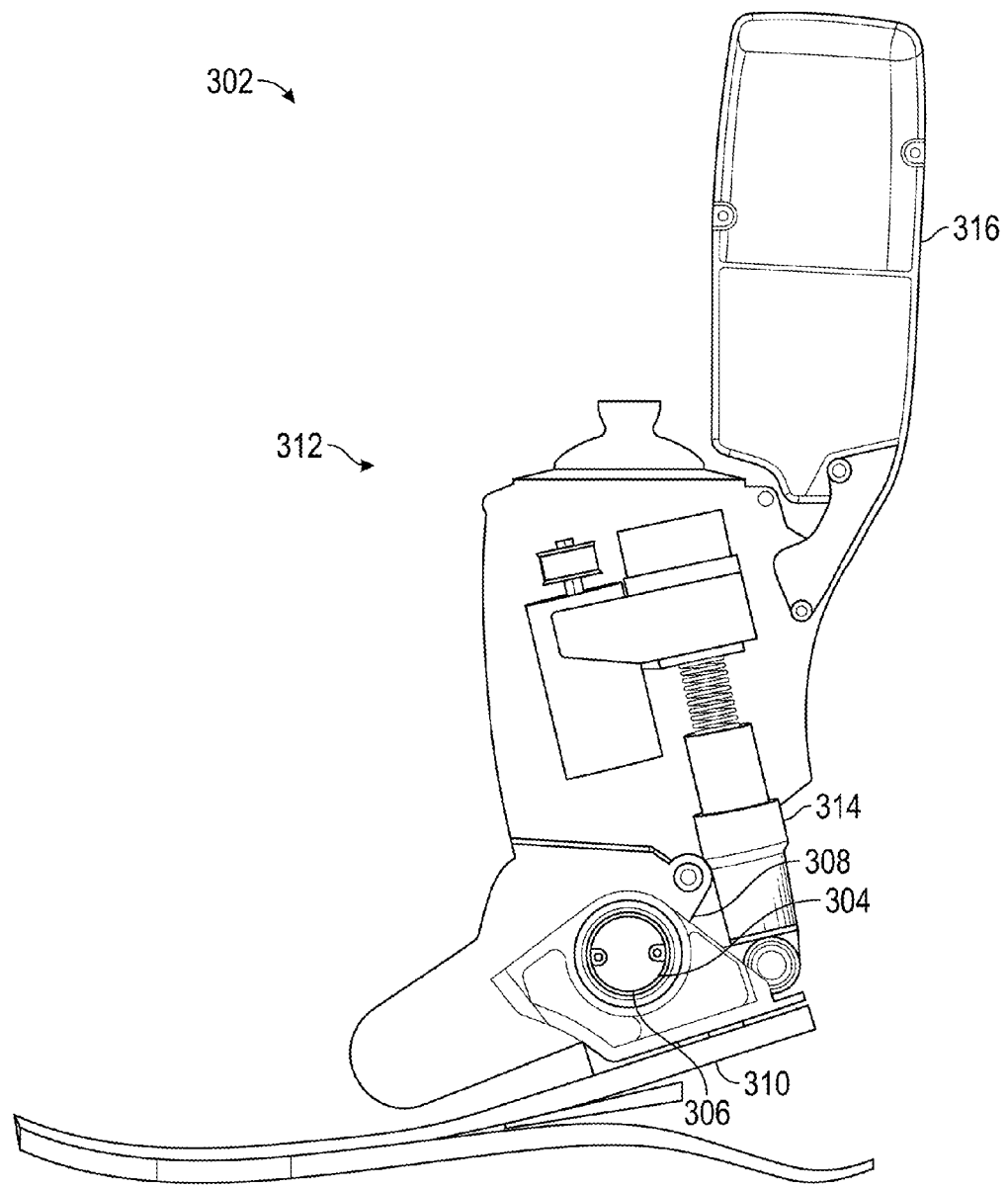
FIG. 24 is a side see-through view of an implementation of an actuator control system.

Such an applied torque to the ankle joint may be achieved using an actuator that rotates a first member relative to a second member. FIG. 24 shows a representative example of an actuator control system 302, which in the example shown is a foot-ankle prosthesis 312 which includes elements of a commercially available foot-ankle prosthesis marketed under the trade name BIOM® by IWALK, INC. of Bedford, Mass. A joint 304 couples a first member (leg member) 308 with a second member (foot member) 310. An actuator 314 is coupled with the joint and is configured to rotate the first member relative to the second member. The joint is therefore a motorized joint 306. A controller 316 may be included in a housing portion that also includes a battery or may be included in or on any other portion of the prosthesis, and may include any software and/or hardware components as will be recognized and understood by the practitioner of ordinary skill in the art. The controller utilizes the control algorithm to provide an input to the actuator, such as a voltage, a current, or any combination thereof, to apply the proper rotation of the first member relative to the second member.

Naturally, although only a single actuator is shown, it is to be understood that any number of actuators acting in concert, in series, in parallel, or even relatively independent of one another could be implemented and controlled by the controller to achieve the desired movement. Any type of actuators may be used, as well. While some actuators have been described above, which use magnetic elements to provide a rotation or movement of the actuator, and while brushed and brushless DC motors have been described, similar and/or other elements (pneumatic, mechanical, electromechanical, electromagnetic, and the like) could be used to implement the actuator(s). The actuators, similarly, may provide any type of movement, such as translation, rotation, and the like, and this may be used directly on the first and second member or it may be translated to some other type of motion using gears and the like to achieve the desired rotation of the joint. In short, the methods and the actuator control systems disclosed herein are not limited to any specific type of actuator having any specific type of actuation or movement, but generally may be implemented with a wide variety of actuators having a wide variety of actuation mechanisms and movement types, as will be understood by the practitioner of ordinary skill in the art.

The ability to rotate an ankle joint based on a sensed state that the ankle joint/foot prosthesis is in has the ability to assist a user or robot or the like during ambulation, as detailed in greater detail in the references described above that have been incorporated by reference herein. The same concepts and techniques that are representatively illustrated in the drawings and described herein with respect to an ankle joint may, of course, also be applied to motorized joints for other areas of a body, such as a knee joint, and elbow joint, a shoulder joint, a hip joint, a wrist joint, and so forth, based on current or future understanding of practitioners of ordinary skill in the art as to how to apply the muscle model(s) disclosed herein to those joint systems in appropriate ways.

Using the above model(s), an actuator control system may be configured to utilize a force equation that defines a muscular force ($F_m$) to be applied by a virtual muscle tendon unit (MTU) as $F_m = k_{ss}(X_m - X_p) = k_{ts}X_{ts} + F_{ce} + c_{ce}\dot{X}_{ce}$, where $k_{ss}$ is a spring rate of a series spring, $X_m$ is a change in length of the MTU, $X_p$ is a change in length of the viscous damping element, $k_{ts}$ is a spring rate of the titin spring, $X_{ts}$ is a change in length of the titin spring, $F_{ce}$ is a force of the contractile element, $c_{ce}$ is a damping rate of the contractile element, and $\dot{X}_{ce}$ is a damper velocity of the viscous damping element.

Figure 25:
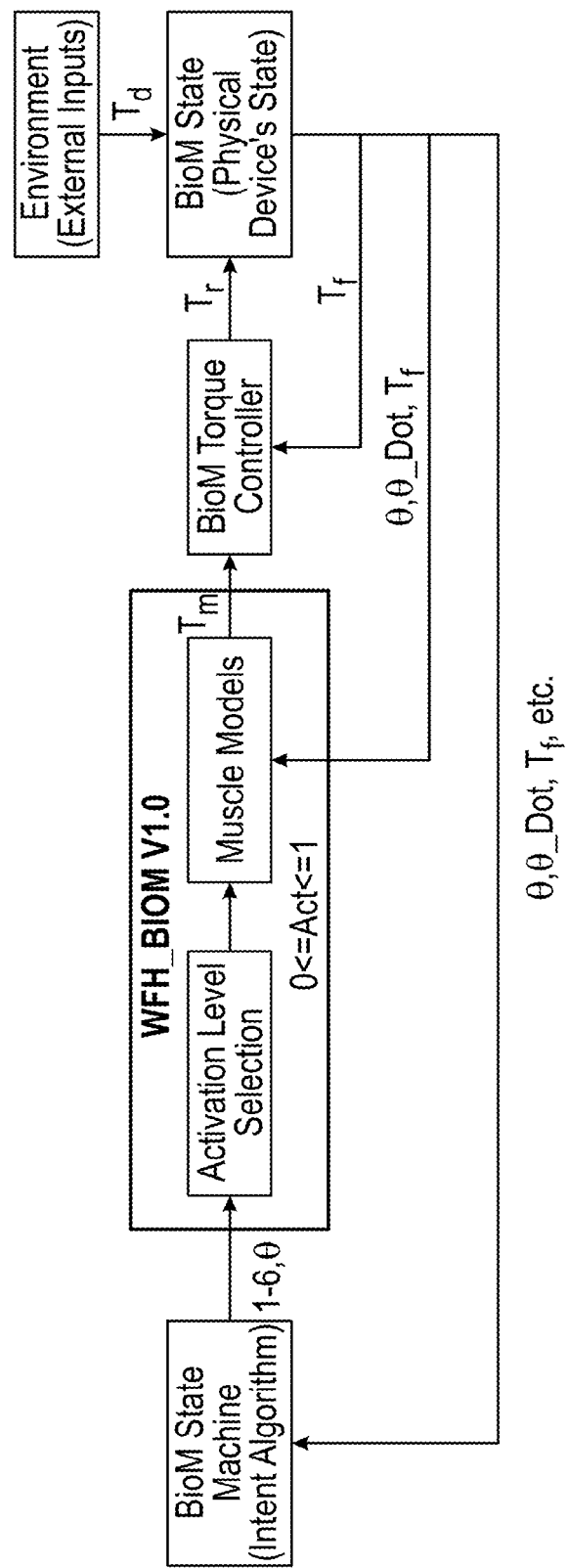
FIG. 25 is a flow chart illustrating features of an implementation of an actuator control system.

FIG. 25 is a representative flow chart representing the functioning of an actuator control system tested on a commercially available foot-ankle prosthesis using a control algorithm as described above and in the references above which have been incorporated by reference. The commercially available foot-ankle prosthesis was one marketed under the trade name BIOM® by IWALK, INC. of Bedford, Mass. The BIOM device had existing control architecture to determine, from the environment (external inputs) a physical state of the system. Control software of the BIOM device was removed and replaced with software implementing a muscle-based model as shown within the area labeled WFH_BIOM V1.0.

The flow chart of FIG. 25 includes a box labeled "Activation Level Selection." These were activation levels of the MTUs chosen to be used for the model to determine a torque for the ankle. For example, in some experiments the virtual anterior muscle (dorsiflexor) was activated at 50% of its maximum force during swing and the virtual posterior muscle (plantar flexor) was activated at 50% of its maximum force during stance. At other times either muscle may be activated at more or less than this, based on the desired torque on the ankle joint. Thus, in implementations any activation level from 0% to 100% may be utilized for either muscle to achieve desired torque at the joint. In some implementations for simplification only one or a few discrete levels may be chosen, such as only activating the dorsiflexor at 50% when it is activated and 0% when not activated, and activating the plantar flexor in a similar manner. The practitioner of ordinary skill in the art will readily understand how to implement such features in an actuator control system and will realize that including more activation levels may include a more complex mathematical model in some ways, but such differences in control algorithms are within the skill level of the practitioner of ordinary skill in the art without undue experimentation by beginning with the base control algorithms disclosed herein and in the references incorporated by reference above.

Referring still to FIG. 25, the system shown utilizes the external inputs, such as torque disturbance ($T_d$), to determine a physical state that the device is in (for example, a rotation of the ankle, a force level on the foot, an external torque on the ankle etc.). Torque disturbance may be measured directly from torque sensors, or in any other manner. The system may use the sensed torque disturbance and/or other sensed parameters to provide torque feedback ($T_f$) to the torque controller. The system may also use the torque feedback, the ankle angle and ankle angle change rate ($\theta$, $\theta$_dot) and/or other elements to determine variables and other inputs for the muscle model(s), such as inputs for one or more mathematical algorithm that models muscle actuation based, at least in part, by the winding filament hypothesis (WFH).

The system may also use the torque feedback, the ankle angle and ankle angle change rate (θ,θ_dot) (and/or other elements) to, using a finite state machine/intent algorithm, determine which of a number of finite states the device is in (represented as 1-6, such as early swing, late swing, etc. described above). The software element WFH_BIOMV1.0 utilizes the determined state (in this case one of six finite states) and the ankle angle θ to select an activation level, which may be a value between 0 and 1 as shown, and this may further be utilized to modify and/or provide input for the muscle model(s) to determine a predicted/requested torque ($T_m$). The torque controller (BioM Torque Controller) may then, utilizing the $T_m$ (torque predicted/requested by muscle model) and $T_f$ (torque feedback from physical state as calculated from sensors), provide $T_r$, a torque requested/applied by BioM's torque controller.

The flowchart shown in FIG. 25 is only a representative example and could be modified in a number of ways to implement an actuator control system in a different manner. In some implementations the finite state machine may be excluded altogether and the control algorithm could utilize the sensed inputs to determine torque to be applied to the joint without determining a state from a number of finite states, and using only a single equation. In such implementations the control algorithm may use the winding filament model to determine when, and how much, to activate each virtual muscle, and the related current, voltage or combination thereof, to send to the actuator(s) or motor of the actuator to effect the desired torque/rotation at each time step such as to effect dorsiflexion and plantar flexion. Thus the control algorithm and/or the mathematical model may in some cases not include a finite state machine. In implementations a control algorithm may further account for internal resistance/friction of a motor and any other element(s) of the system, such as ball screws, moving components, and the like.

An actuator control system as described above may be used to assist ambulation during level walking, a downward incline, an upward incline, upward ascent of stairs, downward ascent of stairs, unlevel terrain, running, jogging, and the like. In short, the control algorithm may generate feedback for torque control for all intended activities and terrain variations. Some commercially available foot-ankle prostheses limit dorsiflexion, such as to 0.5 degrees, which may limit the effectiveness of an actuator control system particularly during stair descent. In some implementations an actuator control system may be implemented with a dorsiflexion limit of at least 2.0 degrees to achieve more effective downward stair descent.

The mathematical model of the control algorithm, as described above, may adapt instantaneously to changes in load, similar to the actual behavior of muscles that, in some cases, have instantaneous reactions to forces instead of waiting for a control signal from the nervous system (which it is theorized is due at least in part to the behavior of titin as described herein).

In implementations a control algorithm as disclosed herein may not be based mainly on the traditional sliding filament (Hill) model, but instead on the winding filament model or winding filament hypothesis (WFH). As described herein, the winding filament model may be used to control a powered prosthesis (i.e., not a prosthesis that is simply passive or relies only on energy storage and return). The WFH model may be based on actual muscle measurements and data gathered from laboratory muscle testing.

As is described in some of the references incorporated by reference herein, the sliding filament (Hill) model of muscle actuation does not predict history dependent muscle properties such as residual force enhancement, force depression, or eccentric negative work. A model of muscle actuation based on the winding filament hypothesis, however, does predict such history dependent muscle properties. A control algorithm based on the winding filament hypothesis thus emulates the intrinsic properties of muscle that characterize biological actuation and models the non-linear properties of muscle during active stretch and shortening.

In implementations a mathematical model may model a non-linear relationship of muscle force to muscle length during muscle stretch and during muscle shortening. The mathematical model may also model powered plantar flexion activation in relation to an angular velocity of the first member relative to the second member during controlled dorsiflexion.

Without being bound by any specific theory, it appears from experimentation and modeling that the winding filament theory (WFT) accurately models muscle behavior as described herein and in the references which are incorporated by reference.

As described above, actuator control systems are described in greater detail in the references above which are incorporated by reference herein, and actuator control systems and implementing components and methods as disclosed herein and as claimed may therefore including any elements, details, features, components, methods, and the like, of any of the references which have been incorporated herein by reference.

In places where the description above refers to particular implementations of actuator control systems and related methods and implementing components, sub-components, methods and sub-methods, it should be readily apparent that a number of modifications may be made without departing from the spirit thereof and that these implementations, implementing components, sub-components, methods and sub-methods may be applied to other actuator control systems and related methods.

What is claimed is:

1. An actuator control system, comprising:
    a motorized joint comprising a first member and a second member rotatable relative to the first member;
    an actuator coupled with the motorized joint and configured to rotate the first member relative to the second member in response to an input comprising one of a voltage, a current, and any combination thereof, and;
    a controller coupled with the actuator and configured to control the input using a control algorithm;
    wherein the control algorithm controls the input based upon a mathematical model of biological muscle actuation that models titin as a filament which winds around actin during muscle actuation.

2. The actuator control system of claim 1, wherein the mathematical model models an N2A region of titin binding to actin during muscle actuation.

3. The actuator control system of claim 1, wherein the mathematical model comprises mathematical representations of a contractile element, a viscous damping element in parallel with the contractile element, and a spring in series with the contractile element through a pulley and simultaneously in parallel with the contractile element.

4. The actuator control system of claim 1, further comprising a sensor configured to sense a state of the motorized joint from among a plurality of states, and wherein the controller controls the input based upon a sensed state.

5. The actuator control system of claim 4, wherein the plurality of states comprises a standing state, a controlled plantar flexion state, a controlled dorsiflexion state, a powered plantar flexion state, an early swing state, and a late swing state.

6. An actuator control system, comprising:
a motorized joint comprising a first member and a second member rotatable relative to the first member;
an actuator coupled with the motorized joint and configured to rotate the first member relative to the second member in response to an input comprising one of a voltage, a current, and any combination thereof, and;
a controller coupled with the actuator and comprising a control algorithm comprising a mathematical model of biological muscle actuation that comprises mathematical representations of:
a contractile element;
a viscous damping element in parallel with the contractile element, and;
a spring (titin spring) in series with the contractile element through a pulley and simultaneously in parallel with the contractile element;
wherein the controller is configured to generate the input using the mathematical model and data from one or more sensors coupled with the motorized joint.

7. The actuator control system of claim 6, wherein the mathematical model defines a muscular force ($F_m$) of a muscle tendon unit (MTU) as $F_m = k_{ss}(X_m - X_p) = k_{ts}X_{ts} + F_{ce} + c_{ce}\dot{X}_{ce}$, where $k_{ss}$ is a spring rate of a series spring, $X_m$ is a change in length of the MTU, $X_p$ is a change in length of the viscous damping element, $k_{ts}$ is a spring rate of the titin spring, $X_{ts}$ is a change in length of the titin spring, $F_{ce}$ is a force of the contractile element, $c_{ce}$ is a damping rate of the contractile element, and $\dot{X}_{ce}$ is a damper velocity of the viscous damping element.

8. The actuator control system of claim 6, wherein the titin spring of the mathematical model comprises an exponential spring.

9. The actuator control system of claim 6, wherein the mathematical model further comprises a mathematical representation of a second spring in series with the viscous damping element and attached to an axle of the pulley.

10. The actuator control system of claim 6, wherein the mathematical model further comprises a mathematical representation of a clutch configured to selectively prevent rotation, but not translation, of the pulley.

11. The actuator control system of claim 6, wherein the viscous damping element comprises a damping rate that is related to a muscle activation level.

12. The actuator control system of claim 6, wherein the viscous damping element comprises a bi-directional damping rate.

13. An actuator control system, comprising:
a foot-ankle prosthesis comprising a joint, the joint rotatably coupling a first member with a second member;
an actuator coupled with the foot-ankle prosthesis and configured to cause dorsiflexion and plantar flexion of the foot-ankle prosthesis by rotating the first member relative to the second member in response to an input comprising one of a voltage, a current, and any combination thereof, and;
a controller coupled with the actuator and configured to generate the input using a control algorithm;
wherein the control algorithm is based upon a mathematical model of biological muscle actuation that models titin as a filament which winds around actin during muscle actuation.

14. The actuator control system of claim 13, wherein the mathematical model models an N2A region of titin binding to actin during muscle actuation.

15. The actuator control system of claim 13, wherein the mathematical model comprises a mathematical representation of a virtual anterior muscle for effecting dorsiflexion and a virtual posterior muscle for effecting plantar flexion, the virtual posterior muscle modeled after a combination of a soleus muscle and a gastrocnemius muscle.

16. The actuator control system of claim 15, wherein the mathematical model is configured to, using a sensed ankle angular position: calculate a length of the virtual anterior muscle, calculate a length of the virtual posterior muscle, calculate a force produced by the virtual anterior muscle, and calculate a force produced by the virtual posterior muscle.

17. The actuator control system of claim 16, wherein the mathematical model is configured to calculate a net ankle torque using the calculated force produced by the virtual anterior muscle and the calculated force produced by the virtual posterior muscle and, using the calculated net ankle torque, generate the input.

18. The actuator control system of claim 15, wherein the mathematical model comprises a value representing a muscle activation level of the virtual anterior muscle, a value representing a muscle activation level of the virtual posterior muscle, a value related to an attachment parameter of the virtual anterior muscle, and a value related to an attachment parameter of the virtual posterior muscle.

19. The actuator control system of claim 13, wherein the mathematical model models a non-linear relationship of muscle force to muscle length during muscle stretch and during muscle shortening.

20. The actuator control system of claim 13, wherein the mathematical model models powered plantar flexion activation in relation to an angular velocity of the first member relative to the second member during controlled dorsiflexion.

* * * * *

UNITED STATES PATENT AND TRADEMARK OFFICE
CERTIFICATE OF CORRECTION

Page 1 of 1

PATENT NO. : 10,154,915 B2
APPLICATION NO. : 14/880118
DATED : December 18, 2018
INVENTOR(S) : Kiisa Nishikawa, John Tester and Jeremy Petak It is certified that error appears in the above-identified patent and that said Letters Patent is hereby corrected as shown below:

In the Specification

Column 20, Line 17, delete "filaments upon Ca' influx", insert --filaments upon $Ca^{2+}$ influx--

Signed and Sealed this
Fifth Day of March, 2019

Andrei Iancu
*Director of the United States Patent and Trademark Office*